US012134785B2

(12) United States Patent
Takasato et al.

(10) Patent No.: US 12,134,785 B2
(45) Date of Patent: Nov. 5, 2024

(54) DIFFERENTIATION OF PLURIPOTENT STEM CELLS TO FORM RENAL ORGANOIDS

(71) Applicant: The University of Queensland, St. Lucia (AU)

(72) Inventors: Minoru Takasato, Moonee Ponds (AU); Melissa Little, Coburg (AU)

(73) Assignee: The University of Queensland, St. Lucia (AU)

( * ) Notice: Subject to any disclaimer, the term of this patent is extended or adjusted under 35 U.S.C. 154(b) by 1093 days.

(21) Appl. No.: 16/682,541

(22) Filed: Nov. 13, 2019

(65) Prior Publication Data

US 2020/0339957 A1    Oct. 29, 2020

Related U.S. Application Data

(63) Continuation of application No. 15/536,018, filed as application No. PCT/AU2015/050798 on Dec. 15, 2015, now abandoned.

(30) Foreign Application Priority Data

Dec. 15, 2014    (AU) ................................ 2014277667

(51) Int. Cl.
    *C12N 5/071*    (2010.01)
    *C12N 5/074*    (2010.01)
(52) U.S. Cl.
    CPC ......... *C12N 5/0687* (2013.01); *C12N 5/0686* (2013.01); *C12N 5/0696* (2013.01); *C12N 2501/119* (2013.01); *C12N 2501/155* (2013.01); *C12N 2501/16* (2013.01); *C12N 2501/385* (2013.01); *C12N 2501/415* (2013.01); *C12N 2506/02* (2013.01); *C12N 2506/45* (2013.01)
(58) Field of Classification Search
    CPC .................................................. C12N 5/0687
    See application file for complete search history.

(56) References Cited

U.S. PATENT DOCUMENTS

| 2005/0244962 A1 | 11/2005 | Thomson et al. |
| 2007/0128174 A1 | 6/2007 | Kleinsek et al. |
| 2012/0116568 A1 | 5/2012 | Murphy et al. |
| 2013/0122536 A1 | 5/2013 | Osafune et al. |
| 2013/0122589 A1 | 5/2013 | Kimber et al. |
| 2013/0164339 A1 | 6/2013 | Murphy et al. |
| 2013/0190210 A1 | 7/2013 | Murphy et al. |
| 2014/0012407 A1 | 1/2014 | Murphy et al. |
| 2014/0363888 A1 | 12/2014 | Osafune et al. |
| 2016/0237409 A1 | 8/2016 | Little et al. |

FOREIGN PATENT DOCUMENTS

| CN | 101072868 A | 11/2007 |
| JP | 2009508650 A | 3/2009 |
| JP | 2014531204 A | 11/2014 |
| WO | 2010007031 A2 | 1/2010 |
| WO | 2012013969 A1 | 2/2012 |
| WO | 2012168167 A1 | 12/2012 |
| WO | 2013040087 A2 | 3/2013 |
| WO | 2013094771 A1 | 6/2013 |
| WO | 2014110590 A1 | 7/2014 |
| WO | 2014197934 A1 | 12/2014 |
| WO | 2015069619 A1 | 5/2015 |
| WO | 2016094948 A1 | 6/2016 |

OTHER PUBLICATIONS

Barak et al., 2012, Developmental Cell, vol. 22, pp. 1191-1207 (Year: 2012).*
Xinaris et al. (2012, J. Americ. Soc. Nephr., vol. 23, pp. 1857-1868) (Year: 2012).*
Lam et al. (Jul. 2014, Semin. Nephrol., vol. 34(4), pp. 445-461). (Year: 2014).*
Schumacher et al. (2021, Regenerative Med., vol. 6:45, pp. 1-11) (Year: 2021).*
Takasato et al. (ePub Dec. 15, 2013, Nature Cell Biology, vol. 16(1), pp. 118-126 + Supplementary Data). (Year: 2013).*
Abu-Abed et al., "The retinoic acid-metabolizing enzyme, CYP26AI, is essential for normal hindbrain patterning, vertebral identity, and development of posterior structures," Genes & Development, Jan. 2001, vol. 15, pp. 226-240.
Briggs et al., "Integration-Free Induced Pluripotent Stem Cells Model Genetic and Neural Developmental Features of Down Syndrome Etiology," Stem Cells, Mar. 2013, vol. 31, pp. 467-478.
Brown et al., "Role for compartmentalization in nephron progenitor differentiation"< PNAS, Mar. 2013, vol. 110, No. 12, pp. 4640-4645.
Brunskill et al., "Atlas of Gene Expression in the Developing Kidney at Microanatomic Resolution," Developmental Cell, Nov. 2008, vol. 15, pp. 781-791.
Brunskill et al., "Defining the Molecular Character of the Developing and Adult Kidney Podocyte," PLoS ONE, Sep. 2011, vol. 6, No. 9, p. e24640, 12 pages.

(Continued)

*Primary Examiner* — Anoop K Singh
*Assistant Examiner* — David A Montanari
(74) *Attorney, Agent, or Firm* — Leon Y. Lum

(57) ABSTRACT

A method is provided for producing renal organoids comprising nephrons, ureteric bud and vasculature and/or progenitors of these. In one embodiment, the methods includes contacting intermediate mesoderm cells with: fibroblast growth factor 9 and/or fibroblast growth factor 20 and/or fibroblast growth factor 2 and optionally, one or more selected from the group consisting of: bone morphogenic protein 7; heparin; a Wnt agonist; retinoic acid; and an RA antagonist under conditions that promote formation of vascularized renal organoids. Another embodiment includes producing mesoderm cells by sequentially contacting pluripotent stem cells with a Wnt agonist and fibroblast growth factor 9 and/or fibroblast growth factor 20 and/or fibroblast growth factor 2, followed by a relatively short re-exposure to the Wnt agonist. The renal organoids may have end uses such as for kidney repair and regeneration, bioprinting of kidneys or functional components thereof, renal cell arrays and screening compounds for nephrotoxicity.

24 Claims, 13 Drawing Sheets

Specification includes a Sequence Listing.

(56) References Cited

OTHER PUBLICATIONS

Cebrian et al., "The Number of Fetal Nephron Progenitor Cells Limits Ureteric Branching and Adult Nephron Endowment," Cell Reports, Apr. 2014, vol. 7, pp. 127-137.
Cheng et al., "Tissue Distribution, Ontogeny, and Hormonal Regulation of Xenobiotic Transporters in Mouse Kidneys," Drug Metabolism and Disposition, Nov. 2009, vol. 37, No. 11, pp. 2178-2185.
Cummings et al., "Cisplatin-Induced Renal Cell Apoptosis: Caspase 3-Dependent and -Independent Pathways," The Journal of Pharmacology and Experimental Therapeutics, Jul. 2002, vol. 302, No. 1, pp. 8-17.
Dobin et al., "STAR: ultrafast universal RNA-seq aligner," Bioinformatics, Oct. 2012, vol. 29, No. 1, pp. 15-21.
Duester, Gregg, "Retinoic Acid Synthesis and Signaling During Early Organogenesis," Cell, Sep. 2008, vol. 134, No. 6, pp. 921-931.
Floege et al., "Localization of PDGF a-receptor in the developing and mature human kidney," Kidney International, Apr. 1997, vol. 51, No. 4, pp. 1140-1150.
International Search Report for International Application No. PCT/AU2015/050798, mailed on Apr. 27, 2016, 7 pages.
James et al., "Patterning of the Avian Intermediate Mesoderm by Lateral Plate and Axial Tissues," Dev. Biol, Jan. 2003, vol. 253, pp. 109-124.
Kang et al., "Differentiation of human pluripotent stem cells into nephron progenitor cells in a serum and feeder free system," PLoS One, Apr. 2014, vol. 9, p. e94888, 11 pages.
Kobayashi et al., "Identification of a Multipotent Self-Renewing Stromal Progenitor Population during Mammalian Kidney Organogenesis," Stem Cell Reports, Oct. 2014, vol. 3, pp. 650-662.
Lam et al., "Rapid and Efficient Differentiation of Human Pluripotent Stem Cells into Intermediate Mesoderm that Forms Tubules Expressing Kidney Proximal Tubular Markers," J. Am. Soc. Nephrol., Jun. 2014, vol. 25, No. 6, pp. 1211-1225.
Loughna et al., "Effects of oxygen on vascular patterning in Tie I/Lacz Metanephric kidneys in vitro," Biochem. Biophys. Res. Commun., Jun. 1998, vol. 247, No. 2, pp. 361-366.
Love et al., "Moderated estimation of fold change and dispersion for RNA-seq data with DESeq2," Genome Biol, Dec. 2014, vol. 15, p. 550, 21 pages.
Mae et al., "Monitoring and robust induction of nephrogenic intermediate mesoderm from human pluripotent stem cells," Nat. Commun., Jan. 2013, vol. 4, pp. 1-11.
Mese et al., "The role of caspase family protease, caspase-3 on cisplatin-induced apoptosis in cisplatin 30 resistant A43 I cell line, " Cancer Chemother. Pharmacol., Sep. 2000, vol. 46, pp. 241-245.
Mugford et al., "Osr1 expression demarcates a multi-potent population of intermediate mesoderm that undergoes progressive restriction to an Osr1-dependent nephron progenitor compartment within the mammalian kidney," Dev. Biol., Dec. 2008, vol. 324, pp. 88-98.
Murphy et al., "3D bioprinting of tissues and organs," Nat. Biotechnol., Aug. 2014, vol. 32, pp. 773-785.
Naujok et al., "The Generation of Definitive Endoderm from Human Embryonic Stem Cells is Initially Independent from Activin A but Requires Canonical Wnt-Signaling," Stem Cell Rev. Rep., Jun. 2014, vol. 10, pp. 480-493.
Orlova et al., "Generation, expansion and functional analysis of endothelial cells and pericytes derived from human pluripotent stem cells," Nat Protoc., May 2014, vol. 9, No. 6, pp. 1514-1531.
Park et al., "Six2 and Wnt regulate self-renewal and commitment of nephron progenitors through shared gene regulatory networks," Dev. Cell, Sep. 2012, vol. 23, pp. 637-651.
Roost et al., "KeyGenes, a Tool to Probe Tissue Differentiation Using a Human Fetal Transcriptional Atlas," Stem Cell Reports, Jun. 2015, vol. 4, No. 6, pp. 1112-1124.
Sakai et al., The retinoic acid-inactivating enzyme CYP26 is essential for establishing an uneven distribution of retinoic acid along the anterior-posterior axis within the mouse embryo, Genes & Development, Jan. 2001, vol. 15, pp. 213-225.
Short et al., "Global quantification of tissue dynamics in the developing mouse kidney," Dev. Cell, Apr. 2014, vol. 29, pp. 188-202.
Sims-Lucas et al., "Endothelial Progenitors Exist within the Kidney and Lung Mesenchyme," PLoS One, Jun. 2013, vol. 8, No. 6, p. e65993, 8 pages.
Sweetman et al., "The migration of paraxial and lateral plate mesoderm cells emerging from the late primitive streak is controlled by different Wnt signals," BMC Dev. Biol., Jun. 2008, vol. 8, pp. 1-15.
Taguchi, A., et al., "Redefining the In Vivo Origin of Metanephric Nephron Progenitors Enables Generation of Complex Kidney Structures from Pluripotent Stem Cells," Cell Stem Cell, Jan. 2014, vol. 14, pp. 53-67.
Takasato et al., "'Directing human embryonic stem cell differentiation towards a renal lineage generates a self- organizing kidney,'" Nature Cell Biology, Dec. 15, 2013, vol. 16, No. 1, pp. 118-127.
Takasato et al., "Kidney organoids from human iPS cells contain multiple lineages and model human hephrogenesis," Nature, Oct. 2015, vol. 526, pp. 564-568.
Takasato et al., "The origin of the mammalian kidney: implications for recreating the kidney in vitro," Development, Jun. 2015, vol. 142, pp. 1937-1947.
Thiagarajan et al., "Identification of anchor genes during kidney development defines ontological relationships, molecular subcompartments and regulatory pathways," PLoS One, Feb. 2011, vol. 6, No. 2, p. e17286, 15 pages.
Xia et al., "Directed differentiation of human pluripotent cells to ureteric bud kidney progenitor-like cells," Nat. Cell Biol., Nov. 2013, vol. 15, No. 12, pp. 1507-1515.
Xinaris et al., "in Vivo Maturation of Functional Renal Organoids Formed from Embryonic Cell Suspensions," JASN, Nov. 2012, vol. 23, pp. 1857-1868.
Xu et al., "Eya1 interacts with Six2 and Myc to regulate expansion of the nephron progenitor pool during nephrogenesis, " Dev. Cell, Nov. 2014, vol. 31, No. 4, pp. 434-447.
Araoka et al., "Efficient and Rapid Induction of Human iPSCs/ESCs into Nephrogenic Intermediate Mesoderm Using Small Molecule-Based Differentiation Methods," PLOS One, Jan. 2014, vol. 9, No. 1, pp. e84881, 14 pages.
Ou et al., "Fibroblast growth factor and organ development", Journal of Clinical Rehabilitative Tissue Engineering Research, Apr. 2011, vol. 15, No. 15, pp. 2800-2804.

* cited by examiner

DIFFERENTIATION OF PLURIPOTENT STEM CELLS TO FORM RENAL ORGANOIDS

TECHNICAL FIELD

THIS INVENTION relates to kidney development. More particularly, this invention relates to an in vitro method of producing renal organoids comprising nephrons and/or ureteric bud and/or progenitors of these, which are at least partly vascularized and contain a renal interstitial compartment.

BACKGROUND

With the prevalence of end stage renal disease rising 8% per annum globally, there is an urgent need for renal regenerative strategies. The kidney is a mesodermal organ that differentiates from the intermediate mesoderm (IM) via the formation of a ureteric bud (UB) and the interaction between this bud and the adjacent IM-derived metanephric mesenchyme (MM). The nephrons arise from a nephron progenitor population derived from the MM. Other progenitors within the IM or MM are regarded as contributing to the renal stroma/interstitium and components of the renal vasculature, including the glomerular capillaries. The IM itself is derived from the posterior primitive streak. While the developmental origin of the kidney is well understood, nephron formation in the human kidney is completed before birth[5]. Hence, there is no postnatal stem cell able to replace lost nephrons.

Human Pluripotent Stem cells have great potential for the generation of a cell-based treatment for kidney disease. However, the realisation of human pluripotent stem cells as a source of cells for clinical use and as a treatment, such as for kidney disease, has been hindered by the lack of understanding of how to produce the necessary cell types that give rise to nephrons and other structures of the kidney.

SUMMARY

The present inventors have successfully directed the differentiation of human pluripotential stem cells through posterior primitive streak and intermediate mesoderm (IM) under fully chemically defined monolayer culture conditions using growth factors used during normal embryogenesis. This differentiation protocol results in the synchronous induction of ureteric bud (UB) and metanephric mesenchyme (MM) that forms a self-organising structure, including nephron formation and segmentation to form distal tubule, proximal tubule and Bowman's capsule, in vitro. Organoids also contain mesenchyme-derived kidney stroma. Such hESC-derived components show broad renal potential ex vivo, illustrating the potential for pluripotent stem cell-based renal regeneration. Further to this, the inventors have directed the differentiation of vasculature within kidney organoids comprising differentiated ureteric bud (UB), metanephric mesenchyme (MM) and MM-derived nephrons and stroma. In a particular form, the invention provides generation of aggregated nephron progenitor cells and ureteric epithelial progenitor cells that form renal organoids in a shortened culture period. More particularly, the invention provides a method for directing human pluripotent stem cells to form a complex multicellular kidney organoid that comprises fully segmented nephrons surrounded by endothelia and renal interstitium and is transcriptionally similar to a human fetal kidney.

Accordingly, one aspect of the invention provides a method of producing nephron progenitor cells and ureteric epithelial progenitor cells, said method including the step of contacting intermediate mesoderm (IM) cells with: fibroblast growth factor 9 (FGF9) and/or fibroblast growth factor 20 (FGF20) and/or fibroblast growth factor 2 (FGF2); and optionally, one or more agents selected from the group consisting of: bone morphogenic protein 7 (BMP7); heparin; a Wnt agonist: retinoic acid (RA), analog or agonist; and an RA antagonist; to thereby produce nephron progenitor cells and ureteric epithelial progenitor cells from the IM cells, under conditions that induce or promote aggregation of nephron progenitor cells and ureteric epithelial progenitor cells into one or more renal organoids whereby the renal organoids are at least partly vascularized and/or comprise vascular progenitor cells.

In some embodiments, at least partial vascularization and/or the presence of vascular progenitor cells is facilitated by conditions that promote or direct development of vascular endothelium or vascular progenitors from mesenchyme cells or tissues.

In one embodiment, vascularization of the renal organoid is facilitated by inclusion of one or more human pluripotent stem cells and/or vascular endothelial progenitors differentiated therefrom.

In another embodiment, vascularization of the renal organoid is facilitated by use of a suitable oxygen tension that facilitates vascularization.

In one embodiment, the IM cells are derived or differentiated from posterior primitive streak cells.

In one embodiment, the posterior primitive streak cells are derived or differentiated from human pluripotent stem cells (hPSCs). Non-limiting examples of hPSCs include human embryonic stem cells (hESCs) and induced human pluripotent stem cells (iPSCs).

A related aspect of the invention provides a method of producing mesoderm cells, said method including the steps of contacting hPSCs with a Wnt agonist to thereby produce mesoderm cells. The mesoderm cells may be a mixed population of mesodermal cells such as definitive mesoderm and intermediate mesoderm (IM) including rostral IM and/or caudal IM.

The method may further include the subsequent step of contacting the definitive mesoderm cells with fibroblast growth factor 9 (FGF9) and/or fibroblast growth factor 20 (FGF20) and/or fibroblast growth factor 2 (FGF2).

Suitably, the subsequent step of contacting the definitive mesoderm cells with fibroblast growth factor 9 (FGF9) and/or fibroblast growth factor 20 (FGF20) and/or fibroblast growth factor 2 (FGF2) step facilitates the formation of intermediate mesoderm (IM) which subsequently gives rise to the differentiation of both ureteric epithelium and nephron progenitor cells from the IM cells.

In a further embodiment, the method further includes the subsequent step of dissociating and reaggregating the cells into a pellet for culture in the presence of FGF2, FGF9 and/or FGF20. Suitably, this step facilitates the production of renal organoids comprising nephrons. The culture in the presence of FGF2, FGF9 and/or FGF20 may be performed on a floating filter at an air/media interface.

In a further embodiment, the method further includes the addition of a Wnt agonist prior to removal of FGF2, FGF9 and/or FGF20 and subsequent culture without growth factors. This step further facilitates the formation of nephrons within renal organoids. Suitably, the Wnt agonist is at relatively high concentration for a relatively short period of time (e.g. 30-60 minutes)

Optionally, culturing cells in the presence of the Wnt agonist, fibroblast growth factor 9 (FGF9) and/or fibroblast growth factor 20 (FGF20) and/or fibroblast growth factor 2 (FGF2) in any of the aforementioned steps may further include one or more of: a retinoic acid (RA) antagonist, RA or RA agonist, bone morphogenic protein 7 (BMP7); and/or retinoic acid.

Preferably, the renal organoids are at least partly vascularized.

Preferably, the renal organoid comprises segmented nephrons surrounded by endothelia, perivascular cells and renal interstitium.

In one embodiment, vascularization of the kidney organoid is facilitated by inclusion of one or more human pluripotent stem cells and/or vascular endothelial progenitors differentiated therefrom.

In another embodiment, vascularization of the kidney organoid is facilitated by use of a suitable oxygen tension that facilitates vascularization.

In one embodiment, the method further includes the step of identifying viable nephron progenitor cells and/or ureteric epithelial progenitor cells.

In certain embodiments, identification of viable nephron progenitor cells and/or ureteric epithelial progenitor cells includes measurement or detection of co-expression of a plurality of nucleic acids and/or proteins as markers for the viable nephron and/or ureteric epithelial progenitor cells.

In another aspect, the invention provides isolated, enriched or purified nephron and/or ureteric epithelial progenitor cells and/or a renal organoid produced according to the method of the aforementioned aspect.

Preferably, the renal organoid comprises segmented nephrons surrounded by endothelia and renal interstitium.

In yet another aspect, the invention provides a method of producing a kidney, or kidney cells or tissues, said method including the step of differentiating kidney, or kidney cells or tissues from the nephron progenitor cells and/or ureteric epithelial progenitor cells and/or the renal organoid of the aforementioned aspects to thereby produce the kidney, or kidney cells or tissues.

In some embodiments, the nephron progenitor cells and/or ureteric epithelial progenitor cells and/or the renal organoid may be used for the recellularisation of whole organ decellularised kidney to thereby create a reconstituted or replacement kidney.

In other embodiments, the nephron progenitor cells and/or ureteric epithelial progenitor cells and/or the renal organoid may be used as a source for cellular therapy of kidney diseases and conditions.

In certain aspects, the nephron progenitor cells and/or ureteric epithelial progenitor cells and/or renal organoids may be used as a source of cells or tissues for bioprinting or bio-engineering whole kidneys, kidney cells and/or tissues for kidney transplant or treating chronic kidney damage or disease.

A particular aspect provides a method of bioprinting a renal structure, said method including depositing a plurality of hPSCs or other progenitor cells disclosed herein to form a renal structure having one or more functional characteristics of a kidney or component thereof, or which is capable of developing one or more functional characteristics of a kidney or component thereof.

Suitably, the renal structure is at least partly vascularized and/or comprises vascular progenitor cells.

Suitably, the hPSCs or other progenitor cells are subjected to a method disclosed herein for producing nephron progenitor cells and ureteric epithelial progenitor cells in the three-dimensional structure.

This particular aspect also provides a bioprinted, renal structure having one or more functional characteristics of a kidney or component thereof, or which is capable of developing one or more functional characteristics of a kidney or component thereof, produced by the aforementioned method.

Another particular aspect provides a method of bioprinting a renal structure, said method including depositing a plurality of nephron progenitor cells and ureteric epithelial progenitor cells disclosed herein to form a renal structure having one or more functional characteristics of a kidney or component thereof, or which is capable of developing one or more functional characteristics of a kidney or component thereof.

Suitably, the bioprinted renal structure is at least partly vascularized and/or comprises vascular progenitor cells.

Suitably, the nephron progenitor cells and ureteric epithelial progenitor cells have been produced from hPSCs by a method disclosed herein.

This particular aspect also provides a bioprinted renal structure having one or more functional characteristics of a kidney or component thereof, or which is capable of developing one or more functional characteristics of a kidney or component thereof, produced by the aforementioned method.

Another aspect of the invention provides an array of nephron progenitors and ureteric progenitors having a planar geometry.

The array may comprise 2-15 or more stacked arrays.

The arrays may stacked in a tessellated pattern.

A related aspect of the invention provides a renal organoid obtained by maturing or differentiating the array, or cells therein, of the aforementioned aspect.

Suitably, the renal organoid is at least partially vascularized and/or comprise vascular progenitors.

In a further aspect, the invention provides a method of determining the nephrotoxicity of one or a plurality of compounds, said method including the step of contacting the one or plurality of compounds with the isolated or purified nephron progenitor cells and/or ureteric epithelial progenitor cells, bioprinted renal structure, array and/or renal organoid of the aforementioned aspects, or kidney cells or tissues differentiated or otherwise obtained therefrom, to thereby determine whether or not the one or plurality of compounds is nephrotoxic.

In one embodiment, this aspect provides bioprinting of the nephron progenitors and/or ureteric epithelial progenitors into kidney organoids for nephrotoxicity screening.

a, Schematic illustrating the developmental pathway from IM to each cellular component of the kidney. CD. collecting ducts; DT, distal tubules; LoH, loops of Henle: PT, proximal tubules; POD, podocytes; VASC, vasculature; STROM, renal interstitium. b-j, Immunofluorescence of kidney organoids at either day 11 or 18. b, Collecting ducts marked by PAX2, GATA3 and ECAD. Scale=50 μm. c,d, Early proximal tubules of LTL$^+$ECAD$^-$ at day 11 (Blanked arrowheads). LTL$^+$ECAD$^+$ maturing proximal tubules appear by day 18 (White arrowheads). Scale=100 μm. e, Proximal tubules express Cubilin (CUBN). Scale=50 μm. f, Loops of Henle marked by UMOD and ECAD. Scale=50 μm. g, A developing glomerulus with podocytes marked by WT1 and NPHS1. Scale=50 μm. h, CD31+ endothelia within the renal interstitium. Scale=200 μm. i, Evidence of endothelial invasion into glomeruli at day 18 of culture. Scale=50 μm. j, The kidney interstitium marked by MEIS1. Scale=100 μm. k-m, Transmission Electron Microscopy of kidney organoids. k, A putative distal tubule with relatively sparse short microvilli (m) and tight junctions (tj). l, A putative proximal tubule with a lumen filled with extensive closely packed microvilli characteristic of the brush border (bb). m, Podocytes (p) with characteristic large nuclei and primary (pf) and secondary foot (sf) processes. Data are representative from a minimum of 3 independent experiments.

Figure 10:
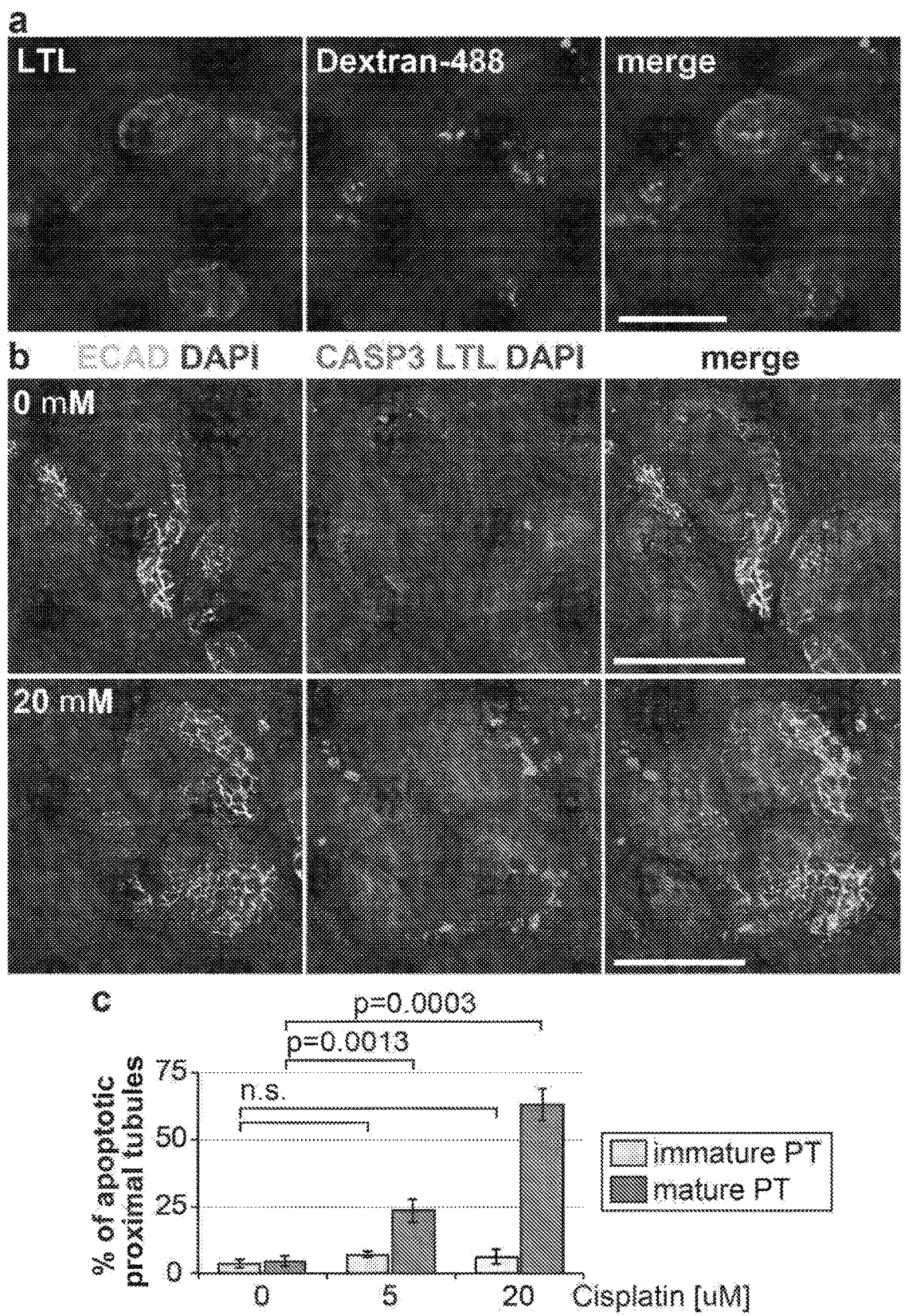

FIG. 10. Functional maturation of the proximal tubule.

a, Dextran uptake assay showing endocytic ability of LTL$^+$ tubules. Scale=50 μm. b, Treating kidney organoids with 20 μM of Cisplatin caused apoptosis in LTL$^+$ECAD$^+$ proximal tubular cells. Apoptotic cells were detected by cleaved Caspase 3 antibody-staining (CASP3). Scale=100 μm. c, Quantification of the number of apoptotic tubules showing mature proximal tubules-specific apoptosis by a nephrotoxicant, Cisplatin. In response to 5 uM and 20 uM Cisplatin, LTL$^+$ECAD$^+$ mature proximal tubules (PT) undervent apoptosis dose-dependently. In contrast, LTL$^+$ ECAD immature PT did not respond to Cisplatin. P values were calculated by independent t-test (mean±s.e., n=5 independent experiments).

Figure 11:
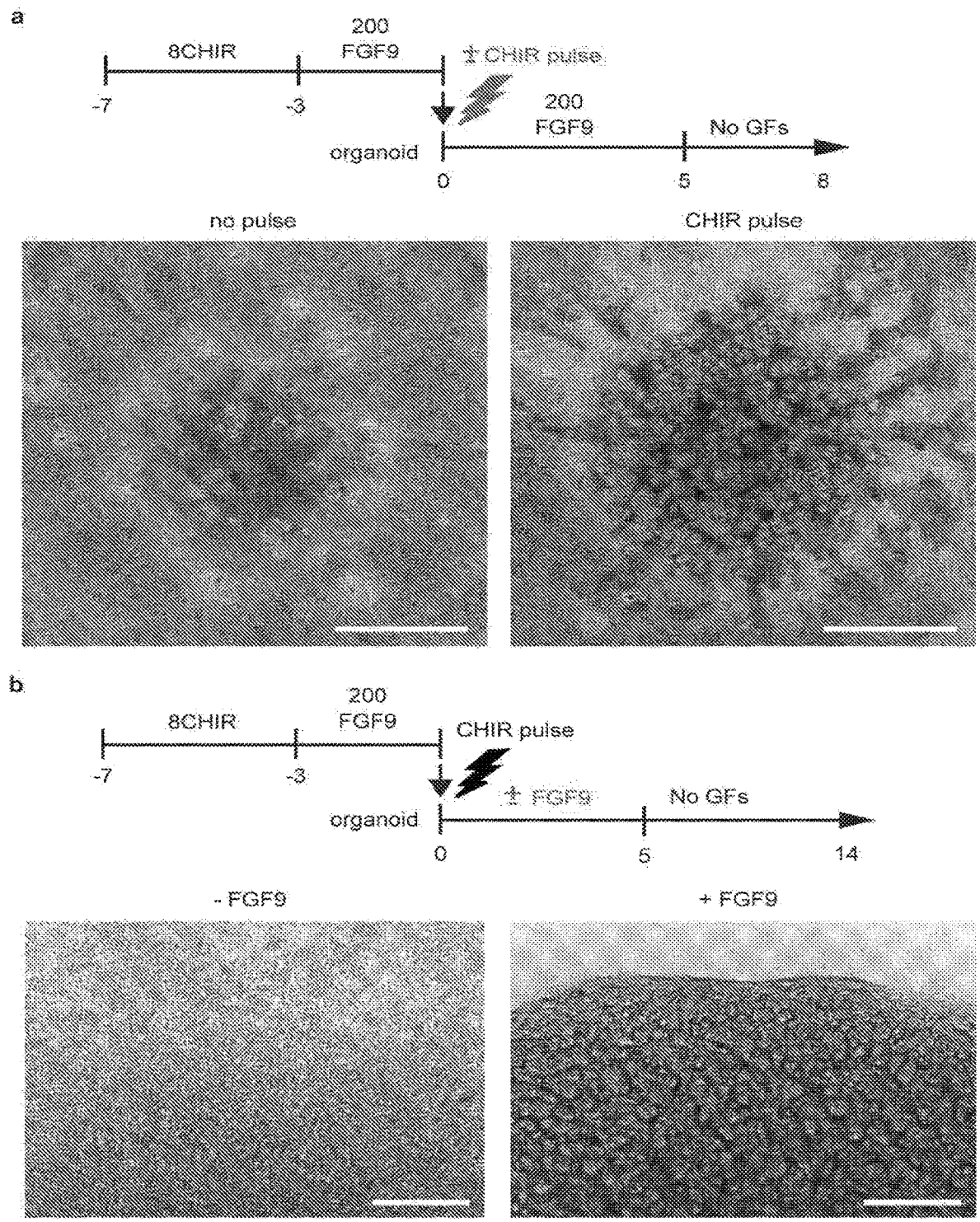

FIG. 11. Regulation of nephrogenesis in the kidney organoid. a, Stimulating organoids with 5 μM of CHIR99021 for 1 h immediately post aggregation promoted nephrogenesis (CHIR pulse), whereas only limited numbers of nephrogenesis events happened without CHIR99021 (no pulse). Scale=1 mm. b, Without the addition of FGF9 after this CHIR99021 pulse, organoids did not initiate nephrogenesis (−FGF9). Scale=200 μm.

Figure 12:
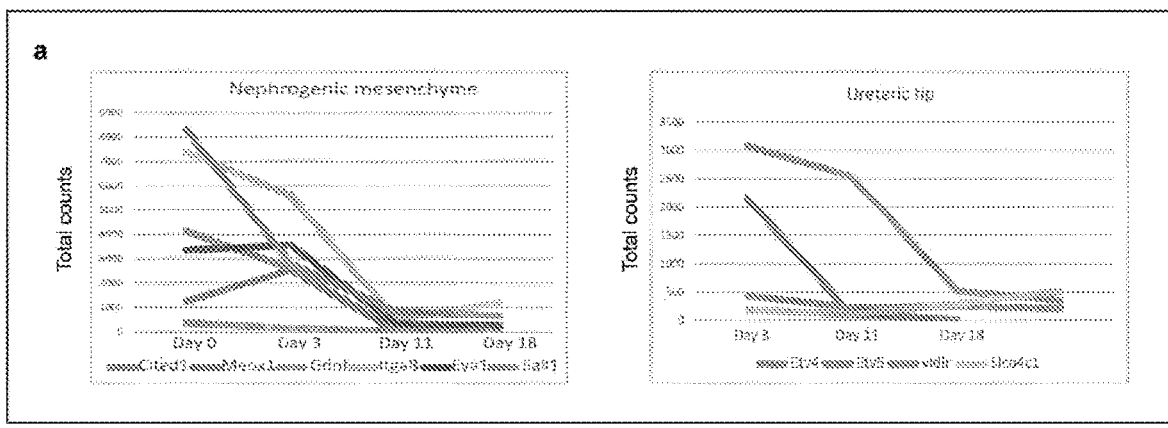
Figure 12:
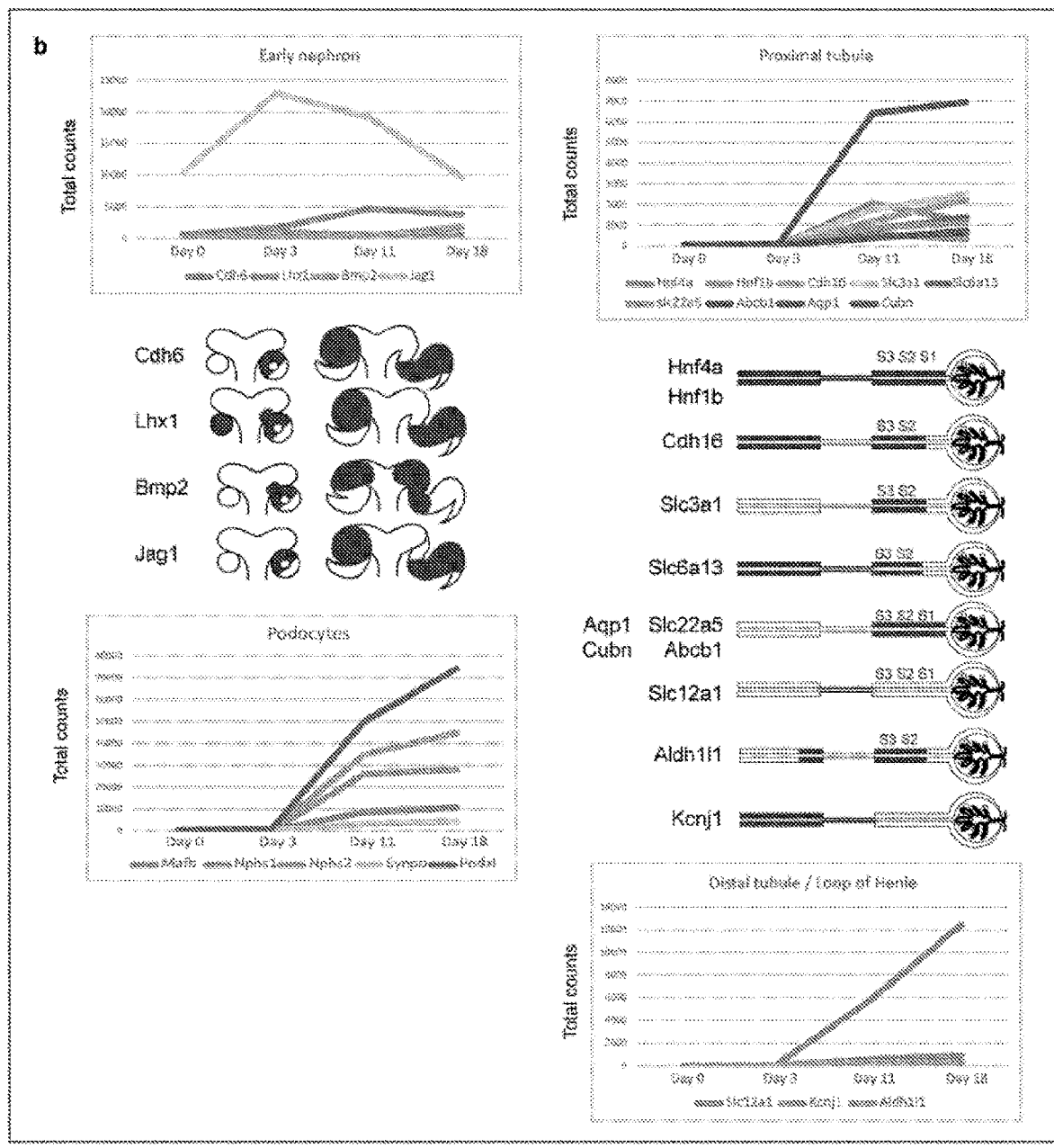
Figure 12:
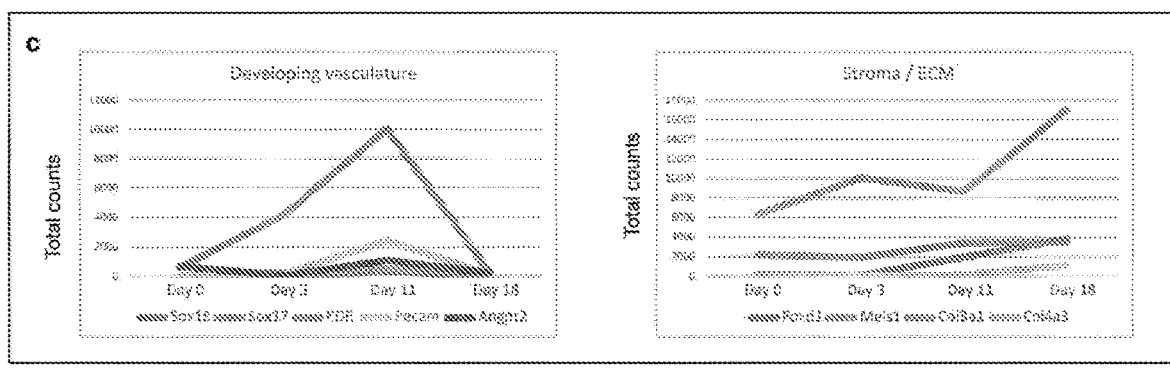

FIG. 12. Changes of gene expression during development of the kidney organoid. a-c, Graphs showing expression changes of selected marker genes at 4 time points (day 0, 3, 11 and 18) of the kidney organoid culture. X-axis represents the count of detection for each gene in an RNA sequencing analysis. Markers of the nephron progenitor (Cap mesenchyme) and collecting duct progenitor (Ureteric tip) were peaked by day 3 then dropped (a). Markers of early nephron increased by day 3, while those of mature nephron components (Proximal and distal tubule and Podocytes) started after day 3. Illustrations show expression regions (blue colored) of each selected gene in the developing kidney (b).

Figure 13:
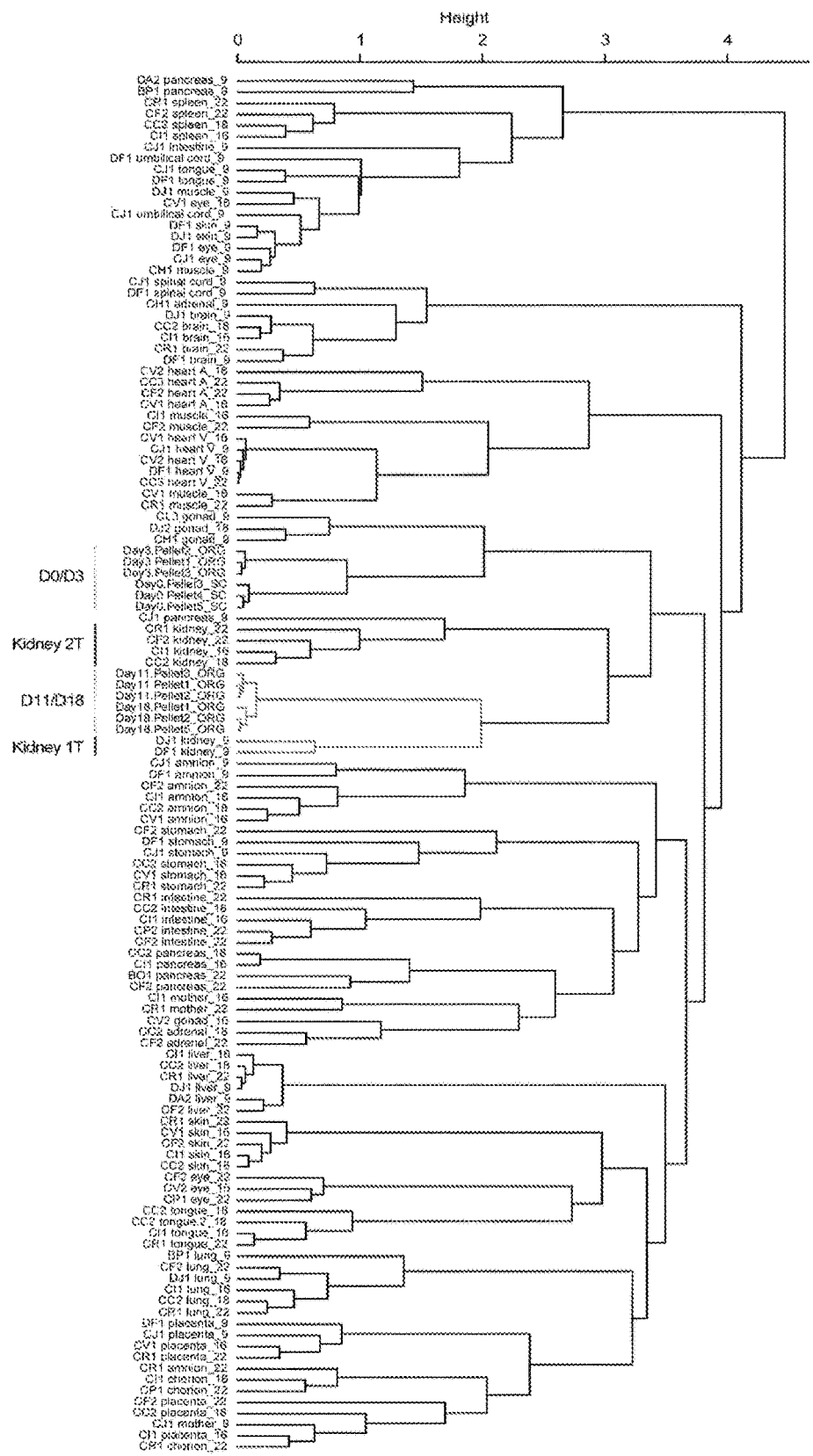

FIG. 13. Dendrogram showing the hierarchical clustering of D0, D3, D11, D18 differentiation experiments and 21 human fetal organs from first and second trimester (GSE66302)[15]. Sample name is composed of individual ID followed by an organ name and gestation week. For instance, 'DJ1 kidney_9' represents a kidney at 9th week gestation from individual ID: DJ1. D0 and D3 kidney organoids cluster with gonad, in agreement with the common origin of both gonad and kidney from the intermediate mesoderm. D11 and D18 kidney organoids show strongest similarity to trimester 1 human kidney. The Classifier genes used for this analysis are detailed in Table 3.

Figure 14:
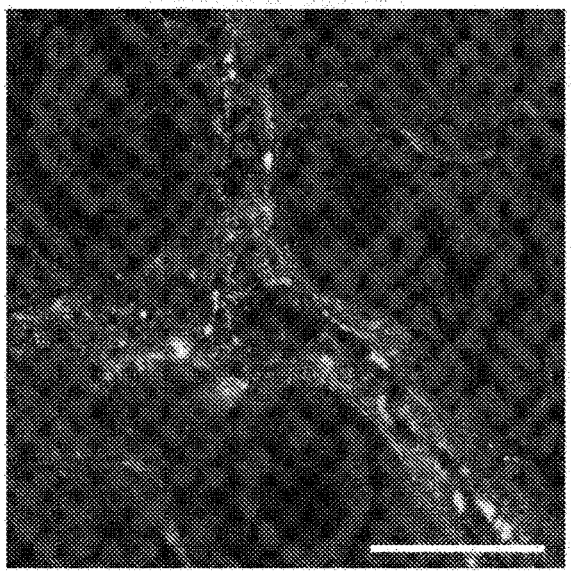
Figure 14:
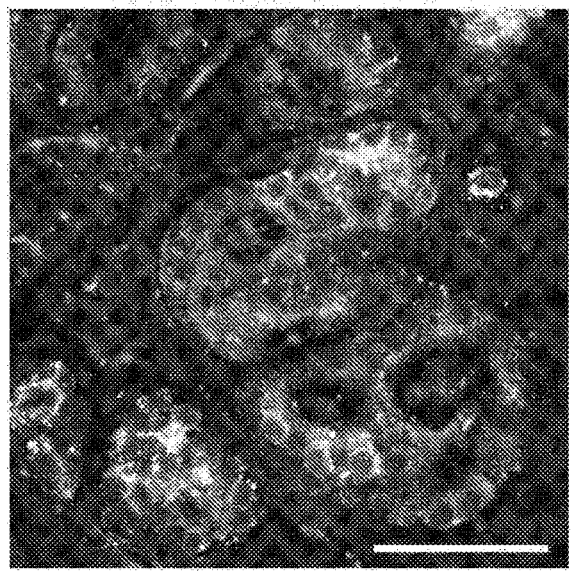

FIG. 14. Characterization of non-epithelial structures in the kidney organoid. All images were taken from day 18 kidney organoids a, PDGFRA$^+$ pericytic cells attaching on KDR$^+$ vessels. Scale=50 µm. b, Some glomeruli contained PDGFRA$^+$ cells likely to represent early mesangial cells[19]. Scale=50 µm.

DETAILED DESCRIPTION

The invention is at least partly predicated on the identification of specific in vitro culture conditions that are tailored to promote the synchronous, simultaneous differentiation of nephron progenitor cells and ureteric epithelial progenitors from intermediate mesoderm (IM) to produce at least partly vascularized renal organoids or other renal cell or tissue aggregates. More specifically, FGF9 plus heparin alone, or in combination with one or more agents including bone morphogenic protein 7 (BMP7), retinoic acid (RA), an RA antagonist: a Wnt agonist: and/or FGF20 plus heparin; and/or FGF2 plus heparin, is capable of facilitating differentiation of intermediate mesoderm into nephron progenitor cells and ureteric epithelial progenitors. Further to this, the in vitro culture method provides a system for differentiating human embryonic stem cells through posterior primitive streak, IM and metanephric mesenchymal stages to produce nephron progenitor cells and ureteric epithelial progenitor cells. Advantageously, the presence or absence of certain molecules such as RA, RA antagonist and/or Wnt agonist can be manipulated to preferentially promote the production of nephron progenitor cells versus ureteric epithelial progenitors, or vice versa. More particularly, the invention is also predicated on the discovery that human pluripotent stem cells may be directed to form a complex multicellular kidney organoid that comprises fully segmented nephrons surrounded by endothelia and renal interstitium and is transcriptionally similar to a human fetal kidney. Vascularization may be facilitated by conditions that promote or direct development of vascular endothelium from mesenchymal cells or tissues.

The nephron progenitor cells and ureteric epithelial progenitor cells are simultaneously induced, direct the differentiation of each other in vivo and are capable of developing into distinct tubular epithelial structures, including ureteric tree and nephron progenitor mesenchyme, during which the epithelial structures substitute for the ureteric tip to maintain the nephron progenitor cells. It is therefore proposed that the hESC-derived ureteric epithelium and/or nephron progenitor cells produced according to the invention may be directed to differentiate into renal cells from both the ureteric and mesenchymal compartments. Furthermore, the capacity of these cells to 'self-organise' into aggregated, organoid structures may therefore be exploited to facilitate kidney repair, such as by way of kidney bioengineering. The nephron progenitor cells, nephrons derived therefrom or kidney organoids "self organized" as described above, may also be suited to nephrotoxicity testing, which has been hampered by a previous inability to produce cells suitable for testing.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described.

As used herein, except where the context requires otherwise, the term "comprise" and variations of the term, such as "comprising". "comprises" and "comprised", are not intended to exclude further additives, components, integers or steps.

It will be appreciated that the indefinite articles "a" and "an" are not to be read as singular indefinite articles or as otherwise excluding more than one or more than a single subject to which the indefinite article refers. For example, "a" cell includes one cell, one or more cells and a plurality of cells.

For the purposes of this invention, by "isolated" is meant material that has been removed from its natural state or otherwise been subjected to human manipulation. Isolated material (e.g., cells) may be substantially or essentially free from components that normally accompany it in its natural state, or may be manipulated so as to be in an artificial state together with components that normally accompany it in its natural state.

By "enriched" or "purified" is meant having a higher incidence, representation or frequency in a particular state (e.g. an enriched or purified state) compared to a previous state prior to enrichment or purification.

The terms "differentiate", "differentiating" and "differentiated", relate to progression of a cell from an earlier or initial stage of a developmental pathway to a later or more mature stage of the developmental pathway. It will be appreciated that in this context "differentiated" does not mean or imply that the cell is fully differentiated and has lost pluropotentiality or capacity to further progress along the developmental pathway or along other developmental pathways. Differentiation may be accompanied by cell division.

A "progenitor cell" is a cell which is capable of differentiating along one or a plurality of developmental pathways, with or without self-renewal. Typically, progenitor cells are unipotent or oligopotent and are capable of at least limited self-renewal.

As will be well understood in the art, the stage or state of differentiation of a cell may be characterized by the expression and/or non-expression of one of a plurality of markers. In this context, by "markers" is meant nucleic acids or proteins that are encoded by the genome of a cell, cell population, lineage, compartment or subset, whose expression or pattern of expression changes throughout development. Nucleic acid marker expression may be detected or measured by any technique known in the art including nucleic acid sequence amplification (e.g. polymerase chain reaction) and nucleic acid hybridization (e.g. microarrays.

Northern hybridization, in situ hybridization), although without limitation thereto. Protein marker expression may be detected or measured by any technique known in the art including flow cytometry, immunohistochemistry, immunoblotting, protein arrays, protein profiling (e.g. 2D gel electrophoresis), although without limitation thereto.

One aspect of the invention provides a method of producing nephron progenitor cells and ureteric epithelial progenitor cells including the step of contacting intermediate mesoderm (IM) cells with: BMP7; retinoic acid (RA); RA antagonist; a Wnt agonist; fibroblast growth factor 9 (FGF9) and/or FGF20; and heparin: to thereby produce nephron progenitor cells and ureteric epithelial progenitor cells from the IM cells.

Reference herein to "retinoic acid" or "RA" includes all forms of retinoic acid (e.g. including all trans RA and 9-cis RA), analogs and/or retinoic acid receptor (RAR) agonists that have a similar biological activity to RA. Various different RA analogs and RAR agonists (including agonists non-selective and selective for RARα, β or γ) are commercially available such as from R & D Systems and Tocris Bioscience.

Specific reference to an "RA antagonist" includes retinoic acid receptor (RAR) antagonists and any other molecule(s) that inhibit, block or prevent RA signalling via the RAR. Non-limiting examples of RAR antagonists include AGN193109, LE 135, ER 50891, BMS 493, BMS 453 and MM 11253, although without limitation thereto. This definition does not exclude the possibility that the RA antagonist also or alternatively mimics a block in signalling via RAR from binding of another ligand.

As used herein a "Wnt agonist" is a molecule that inhibits GSK3 (e.g. GSK3-β) in the context of the canonical Wnt signalling pathway, but preferably not in the context of other non-canonical, Wnt signalling pathways. Non-limiting examples of Wnt agonists include CHIR99021, LiCl SB-216763, CAS 853220-52-7 and other Wnt agonists that are commercially available from sources such as Santa Cruz Biotechnology and R & D Systems. This definition should not be read as absolutely excluding the possibility that the Wnt agonist mimics one or more other inhibitors of GSK3β activity.

It will also be appreciated that fibroblast growth factors such as FGF2, FGF9 and FGF20 may be interchangeable, although FGF9 is preferred. Heparin is typically included to promote or enhance the biological activity of fibroblast growth factors such as FGF2, FGF9 and/or FGF20.

The preferred concentrations of each of FGF9, BMP7, retinoic acid (RA); RA antagonist; Wnt agonist; FGF20 and heparin will be described in more detail hereinafter. Reference will also be made to controlling or manipulating the presence or absence of certain molecules such as RA agonist or analog, RA antagonist and/or Wnt agonist to preferentially promote the production of nephron progenitor cells versus ureteric epithelial progenitors, or vice versa.

As used herein "nephron progenitor cells" are progenitor cells derived from metanephric mesenchyme that can differentiate into all nephron segments (other than collecting duct) via an initial mesenchyme to epithelial transition, which include nephron epithelia such as connecting segment, distal convoluted tubule (DCT) cells, distal straight tubule (DST) cells, proximal straight tubule (PST) segments 1 and 2. PST cells, podocytes, glomerular endothelial cells, ascending Loop of Henle and/or descending Loop of Henle, although without limitation thereto. Nephron progenitor cells are also capable of self-renewal.

Non-limiting examples of markers characteristic or representative of metanephric mesenchyme include WT1, SIX1, SIX2, SALL1, GDNF and/or HOXD11, although without limitation thereto. Non-limiting examples of markers characteristic or representative of nephron progenitor cells include WT1, SIX1, SLX2. CITED1, PAX2, GDNF, SALL1, OSR1 and HOXD11, although without limitation thereto.

By "ureteric epithelial progenitor cell" is meant an epithelial progenitor cell derived, obtainable or originating from mesonephric duct or its derivative ureteric bud that can develop into kidney tissues and/or structures such as the collecting duct.

Non-limiting examples of characteristic or representative markers of ureteric epithelial progenitor cells include HOXB7, cRET, GATA3, CALB1, E-CADHERIN and PAX2, although without limitation thereto.

As hereinbefore described, the nephron progenitor cells and ureteric epithelial progenitor cells are differentiated from intermediate mesoderm (IM) cells is the presence of FGF9 alone or in combination with one or more agents that include BMP7, retinoic acid (RA), agonist or analog, an RA antagonist such as AGN193109 and/or FGF20 and preferably heparin.

By "intermediate mesoderm (IM)" cells is meant embryonic mesodermal cells that arise from definitive mesoderm which in turn is derived from posterior primitive streak and can ultimately develop into the urogenital system. inclusive of the ureter and kidney and other tissues such as gonad. Non-limiting examples of markers characteristic or representative of intermediate mesoderm include PAX2, OSR1 and/or LHX1.

It will also be appreciated that production of IM cells is not meant to imply that the IM cells are a pure or homogeneous population of IM cells without other cell types being present (such as definitive mesoderm). Accordingly. reference to "IM cells" or a "population of IM cells" means that the cells or cell population comprise(s) IM cells.

Suitably, according to the invention IM cells are produced by contacting posterior primitive streak cells with one or more agents that facilitate differentiation of the posterior primitive streak cells into IM cells, as will be described in more detail hereinafter.

Preferably, the IM cells are produced by contacting posterior primitive streak cells with one or more agents that facilitate differentiation of the posterior primitive streak cells into IM cells Typically, the one or more agents include fibroblast growth factor 9 (FGF9) and, optionally, an RA antagonist such as AGN193109 and/or one or more other FGFs such as FGF 2 and/or FGF20.

By "posterior primitive streak (PPS)" cells is meant cells obtainable from, or cells functionally and/or phenotypically corresponding to, cells of the posterior end of a primitive streak structure that forms in the blastula during the early stages of mammalian embryonic development. The posterior primitive streak establishes bilateral symmetry, determines the site of gastrulation and initiates germ layer formation. Typically, posterior primitive streak is the progenitor of mesoderm (i.e. presumptive mesoderm) and anterior primitive streak is the progenitor of endoderm (i.e. presumptive endoderm). Non-limiting examples of markers characteristic or representative of posterior primitive streak include Brachyury (T). A non-limiting example of a marker characteristic or representative of anterior primitive streak is SOX17. MIXL1 may be expressed by both posterior and anterior primitive streak.

It will also be appreciated that production of posterior primitive streak cells is not meant to imply that the posterior primitive streak cells are a pure or homogeneous population of posterior primitive streak cells without other cell types being present. Accordingly, reference to "posterior primitive streak cells" or a "population of posterior primitive streak cells" means that the cells or cell population comprise(s) posterior primitive streak cells.

Suitably, according to the invention posterior primitive streak cells are produced by contacting hPSC cells with one or more agents that facilitate differentiation of the hPSC cells into posterior primitive streak cells, as will be described in more detail hereinafter.

Typically, the one or more agents include bone morphogenic protein 4 (BMP4), Activin A and/or a Wnt agonist such as CHIR99021.

The terms "human pluripotent stem cell" and "hPSC" refer to cells derived, obtainable or originating from human tissue that display pluripotency. The hPSC may be a human embryonic stem cell or a human induced pluripotent stem cell.

Human pluripotent stem cells may be derived from inner cell mass or reprogrammed using Yamanaka factors from many fetal or adult somatic cell types. The generation of hPSCs may be possible using somatic cell nuclear transfer.

The terms "human embryonic stem cell", "hES cell" and "hESC" refer to cells derived, obtainable or originating from human embryos or blastocysts, which are self-renewing and pluri- or toti-potent, having the ability to yield all of the cell types present in a mature animal. Human embryonic stem cells (hESCs) can be isolated, for example, from human blastocysts obtained from human in vivo preimplantation embryos, in vitro fertilized embryos, or one-cell human embryos expanded to the blastocyst stage.

The terms "induced pluripotent stem cell" and "iPSC" refer to cells derivable, obtainable or originating from human adult somatic cells of any type reprogrammed to a pluripotent state through the expression of exogenous genes, such as transcription factors, including a preferred combination of OCT4, SOX2, KLF4 and c-MYC. hiPSC show levels of pluripotency equivalent to hESC but can be derived from a patient for autologous therapy with or without concurrent gene correction prior to differentiation and cell delivery.

More generally, the method disclosed herein could be applied to any pluripotent stem cell derived from any patient or a hPSC subsequently modified to generate a mutant model using gene-editing or a mutant hPSC corrected using gene-editing. Gene-editing could be by way of CRISPR, TALEN or ZF nuclease technologies.

It will be appreciated from the foregoing, that a preferred broad form the invention provides a method that includes the sequential steps of:
(i) contacting hPSCs with one or more agents that facilitate differentiation of the hPSCs into posterior primitive streak cells;
(ii) contacting posterior primitive streak cells with one or more agents that facilitate differentiation of the posterior primitive streak cells into intermediate mesoderm cells; and
(iii) contacting intermediate mesoderm cells with FGF9 and, optionally, one or more of BMP7; retinoic acid; an RA antagonist such as AGN193109; a Wnt agonist such as CHIR99021; FGF20; and heparin; to thereby produce metanephric mesenchyme cells and ureteric epithelial progenitor cells from the intermediate mesoderm cells.

These sequential steps will be described hereinafter as follows.

(i) Differentiating hPSCs into Posterior Primitive Streak

As will be appreciated from the foregoing, hPSCs are contacted with BMP4, Activin A and/or CHIR99021 in a suitable culture medium in the absence of serum, such as APEL differentiation medium (Ng et al., 2008, Nat. Protoc. 3: 768), although without limitation thereto, to thereby produce posterior primitive streak cells that suitably comprise posterior primitive streak cells. The hPSCs may be hESCs or iPSCs.

Suitably, BMP4 is at a concentration of about 5-40 ng/mL and Activin A is at a concentration of about 3-40 ng/mL. In one embodiment the concentration of BMP4 is about 20-35 ng/mL, or more preferably about 30 ng/mL. In one embodiment, the concentration of Activin A is about 5-30 ng/mL or more preferably 10 ng/mL. Suitably, an optimal relative activity ratio is in the range of 3:1 to 1:6 BMP4 to Activin A. Preferably, an optimal relative activity ratio is in the range of 3:1 to 1:1 BMP4 to Activin A.

In some embodiments, a Wnt agonist such as CHIR99021 may be at a concentration in the range of about 0.5 to 50 µM, preferably about 4-30 µM, more preferably about 5-20 µM or advantageously about 8 µM. In certain embodiments, CHIR99021 is present alone, in the absence of BMP4 and Activin A.

The population of stem cells may be cultured in the medium with BMP4, Activin A and/or a Wnt agonist such as CHIR99021 for 36-120 hours.

In some non-limiting embodiments, cells may be contacted for longer periods with BMP4, Activin A and/or CHIR99021 than is required for hESCs. By way of example, cells such as iPSCs may be contacted with BMP4, Activin A and/or CHIR99021 for up to 96-120 hrs.

The culture medium may be changed every 24-48 hrs.

Although not wishing to be bound by theory, contacting hPSCs with BMP4, Activin A and/or a Wnt agonist such as CHIR99021 as disclosed herein results in formation of primitive streak (PS) including posterior primitive streak. This is an initial step towards the generation of mesodermal and endodermal tissue. Typically, differentiation of hPSCs is toward a mixed population of cells that comprises cells expressing markers characteristic of posterior primitive streak (i.e. presumptive mesoderm) and cells expressing markers characteristic of anterior primitive streak (i.e. presumptive endoderm).

Non-limiting examples of markers characteristic of posterior primitive streak (presumptive mesoderm) include Brachyury 7).

A non-limiting example of a marker characteristic of anterior primitive streak (presumptive endoderm) is SOX7.

(ii) Differentiation of Posterior Primitive Streak Cells into Intermediate Mesoderm (IM)

Suitably, posterior primitive streak cells, or a mixed primitive streak population comprising posterior primitive streak cells, are contacted with one or more fibroblast growth factors (FGFs) that at least includes FGF9 and, optionally, FGF2 and/or FGF20 and/or a retinoic acid (RA) antagonist in a suitable culture medium in the absence of serum, such as APEL differentiation medium.

Typically, the retinoic acid signalling antagonist is a retinoic acid receptor (RAR) inhibitor or antagonist such as AGN193109.

Suitably, FGF2, FGF9 and/or FGF20 are at a concentration of about 100 to 400 ng/mL. In a preferred embodiment, FGF2, FGF9 and/or FGF20 are at a concentration of about 150 to 300 ng/ML or advantageously about 200 ng/mL. In one embodiment, the concentration of the RA antagonist (e.g. AGN193109) is about 0.1-10 µM or more preferably 0.5-5 µM.

The cells are contacted with FGF9, alone or together with FGF2 and/or FGF20 and/or RA antagonist (e.g. AGN193109) for at least about 96 hours but not more than about 190-200 hours. Preferably, the cells are contacted with FGF9 alone or with FGF2 and/or FGF20 and/or RA antagonist (e.g. AGN193109) for about 96 hours.

The culture medium may be changed every 40-48 hrs.

In one embodiment, contacting the posterior primitive streak cells (which typically express markers characteristic of posterior primitive streak (presumptive mesoderm) and anterior primitive streak (presumptive endoderm)) with FGF9 alone or together with FGF2 and/or FGF20 results in differentiation of the cells toward a population of cells expressing markers characteristic of intermediate mesoderm (IM). Non-limiting examples of markers characteristic of intermediate mesoderm include PAX2, LHX1 and OSR1.

(iii) Differentiation of Intermediate Mesoderm (IM) into Nephron Progenitors and Ureteric Epithelial Progenitors Suitably, following contacting posterior primitive streak cells with FGF2, FGF9 and/or FGF20, resultant IM cells are contacted with FGF9 alone or in combination with one or more of BMP7, RA, RA antagonist, FGF20, a Wnt agonist and/or heparin in a suitable culture medium in the absence of serum, such as APEL differentiation medium.

Suitably, FGF9 is at a concentration of about 20 ng to 1 µg/mL. In a preferred embodiment, FGF9 is at a concentration of about 50-500 ng/mL, more preferably about 100-300 ng/mL or advantageously about 200 ng/mL. Typically, heparin is included at a concentration of about 0.1-10 µg/mL, preferably about 0.3-5 µg/mL, 0.5-2 µg/mL or advantageously about 1 µg/mL.

In an embodiment, FGF20 is at a concentration of about 20 ng to 1 µg/mL. In a preferred embodiment, FGF 20 is at a concentration of about 50-500 ng/mL, more preferably about 100-300 ng/mL or advantageously about 200 ng/mL.

In an embodiment, FGF2 is at a concentration of about 20 ng to 1 µg/mL. In a preferred embodiment, FGF 2 is at a concentration of about 50-500 ng/mL, more preferably about 100-300 ng/mL or advantageously about 200 ng/mL.

It will be appreciated that FGF20 and FGF2 may replace or supplement FGF9, as these agents have similar biological activities.

In an embodiment, BMP7 is at a concentration of about 25 to 75 ng/mL. In a preferred embodiment, BMP7 is at a concentration of about 35-60 ng/mL, 45-55 ng/mL or advantageously about 50 ng/mL.

In an embodiment, RA is at a concentration of about 10 µM to 1 µM. In a preferred embodiment, RA is at a concentration of about 30 µM to 0.5 µM, more preferably about 50 µM to 0.2 µM or advantageously about 0.1 µM. Although not binding on the present invention, preliminary data suggest that higher concentrations of RA promote a relative increase in the proportion of ureteric epithelial progenitor cells and that lower concentrations of RA promote a relative decrease in the proportion of ureteric epithelial progenitor cells.

In an embodiment, an RA antagonist such as AGN193109 is at a concentration of about 50 pM to 10 µM. In a preferred embodiment, AGN193109 is at a concentration of about 0.01 µM to 5 µM, more preferably about 0.1 µM to 5 µM or advantageously about 1 µM. Although not binding on the present invention. preliminary data suggest that higher concentrations of AGN193109 promote a relative increase in the proportion of metanephric mesenchyme cells.

In an embodiment, a Wnt agonist such as CHIR99021 is present at a concentration in the range of about 0.1 µM to 10 µM, preferably about 0.2 µM to 5 µM or more preferably at about 1-2 µM.

Although not binding on the present invention, the Wnt agonist promotes a relative increase in the production of nephron progenitor cells from the IM cells. Preferably, cells are contacted with FGF9 alone or together with one or more of BMP7, RA. Wnt agonist, RA antagonist and/or FGF20 and/or FGF2 plus heparin for at least 72 hours but not more than 360 hours. Preferably, the cells are contacted for about 160-220 hrs or more preferably for about 190-200 hours.

The culture medium may be changed every 48-72 hrs.

Typically, contacting intermediate mesoderm cells with FGF9 alone or together with one or more of BMP7, RA, an RA antagonist; a Wnt agonist and/or FGF20 and/or FGF2 and preferably heparin, as disclosed herein, differentiates the intermediate mesoderm cells into cells of metanephric mesenchyme and ureteric epithelium cell lineages. The metanephric mesenchyme lineage includes nephron progenitor cells that are optimally produced after about 72 hrs of culture in FGF9 and heparin. It is also proposed that the presence, absence and/or concentration of RA analog or agonist and/or RA antagonist may be chosen to manipulate the relative amount of ureteric epithelium that is produced by the method, compared to metanephric mesenchyme that is produced by the method. As described previously, RA promotes the formation of ureteric epithelium at the expense of metanephric mesenchyme, whereas an RA antagonist such as AGN193109 promotes the formation of metanephric mesenchyme at the expense of ureteric epithelium. A Wnt agonist such as CHIR99021 may also promotes the survival and/or formation of metanephric mesenchyme at the expense of ureteric epithelium.

Non-limiting examples of markers characteristic or representative of cells of the metanephric mesenchyme lineage or cells thereof include WT1, SIX1, SLX2, SALL1, GDNF and/or HOXD11, although without limitation thereto.

Non-limiting examples of markers characteristic or representative of nephron progenitor cells include WT1, SIX2, CITED1, PAX2, GDNF SALL1 and HOXD11, although without limitation thereto.

Non-limiting examples of markers characteristic or representative of cells of the ureteric epithelial lineage include HOXB7, GATA3, CALB1, E-CADHERIN, PAX2 and/or cRET, although without limitation thereto.

Nephron progenitor cells are likely to be maximally generated 11-15 days, or advantageously 14 days (range of day 11 to 15) after commencement of the method from the start of hPSC cell culture, based upon the co-expression of WT1, SIX2, CITED1, PAX2, GDNF, SALL1 and HOXD11.

Ureteric epithelial progenitor cells may be maximally generated after at least 10 days, or advantageously 14 days after commencement of the method from the start of hPSC culture, based upon the co-expression of HOXB7. cRET. E-CADHERIN and PAX2.

In a preferred form of the method, FGF9 is present for at least part of, or entirely throughout, both steps (ii) and (iii) described herein. More preferably, a Wnt agonist such as CHIR99021 is present for at least part of step (i) described herein.

A particularly preferred method therefor includes the sequential steps of:
(a) contacting human pluripotent stem (hPCS) cells with CHIR99021 to facilitate differentiation of the hPSC cells into posterior primitive streak cells:

(b) contacting the posterior primitive streak cells with FGF9, alone or together with an RA antagonist such as AGN193109, to facilitate differentiation of the posterior primitive streak cells into IM cells; and (c) contacting the IM cells with FGF9 and heparin, alone or together with an RA antagonist such as AGN193109, to thereby produce nephron progenitor cells and ureteric epithelial progenitor cells from the IM cells.

According to this preferred form, it is possible to facilitate kidney differentiation from an initial population of hES cells in a total culture period of about 18-20 days.

Rapid Generation of Renal Organoids from hPSCs

A related aspect of the invention provides a method of producing definitive mesoderm cells, said method including the steps of contacting hPSCs with a Wnt agonist for a more prolonged period (optimally 3-5 days). Suitably, the method of this aspect produces a mesoderm cell population that comprises one or more of definitive mesoderm cells and IM cells, which may include both rostral and caudal IM. Typically, the longer the duration of culture with Wnt agonist, the more caudal IM arises and the less rostral IM persists.

In one embodiment, the method further includes the subsequent step of contacting the mesoderm cells with fibroblast growth factor 9 (FGF9) and/or fibroblast growth factor 20 (FGF20) and/or fibroblast growth factor 2 (FGF2). Suitably, this step facilitates the differentiation of caudal and rostral IM. Suitably, the caudal and rostral IM will in turn differentiate to nephron progenitor cells and ureteric epithelial cells respectively. As previously described, inclusion of RA or an analog or agonist may increase the relative production of ureteric epithelial progenitor cells.

In another embodiment, after contacting the intermediate mesoderm (IM) cells with fibroblast growth factor 9 (FGF9) and/or fibroblast growth factor 20 (FGF20) and/or fibroblast growth factor 2 (FGF2), the method further includes the subsequent step of dissociating and reaggregating the cells. This may be performed in culture on a floating filter at an air-media interface. Suitably, this step facilitates the formation of renal organoids containing nephrons, stroma and vasculature.

In another embodiment, after forming an aggregate for culture (such as on a floating filter), the method further includes the subsequent addition of a Wnt agonist for 30-60 minutes. Suitably, this step facilitates the production of aggregated, renal organoids with maximal nephrons.

It will be appreciated that a preferred object of the method is to produce aggregated, differentiated nephron progenitor cells and ureteric epithelial progenitor cells that form an organoid or other at least partly organized, renal structure. Preferably, the presence of all segments of a normal developing nephron may be present in the organoid, including collecting duct (phenotypically GATA3$^+$ECAD$^+$), early distal tubule (phenotypically GATA3$^-$LTL$^-$ECAD$^+$), early proximal tubule (phenotypically LTL$^+$ECAD$^-$) and glomerulus (phenotypically WT1$^+$). suggestive of normal embryonic organogenesis.

In one embodiment, formation of an aggregate of differentiated cells for culture as an organoid may be achieved in about 7 days culture as described above.

A preferred concentration of a Wnt agonist (e.g. CHIR99021) is about 1-50 mM, preferably about 1-20 µM, 5-15 µM or advantageously about 8 µM. Preferably, the duration of contact with the Wnt agonist is about 4 days.

Suitably, FGF9 is at a concentration of about 20 ng to 1 µg/mL. In a preferred embodiment, FGF9 is at a concentration of about 50-500 ng/mL, more preferably about 100-300 ng/mL or advantageously about 200 ng/mL. Preferably, the duration of subsequent contact with FGF9/FGF20/FGF2 includes heparin for about 3 days.

Preferably, the subsequent addition of a short pulse of a Wnt agonist such as CHIR99021 is immediately upon reaggregation following culture in FGF9/FGF20/FGF2 plus heparin. A preferred concentration of a Wnt agonist (e.g. CHIR99021) is about 1-15 µM, preferably about 2-10 µM or advantageously about 5 µM. The short pulse is typically between 0.5 and 2 hr, such as about 45 minutes or 1 hr.

The formation of aggregated, at least partly organized structures such as renal organoids may be assisted by maintaining or facilitating physical contact between the cultured cells. In this regard, pelleting of the cells prior to addition of the "short pulse" of Wnt agonist (e.g. CHIR99021) may assist organoid formation.

Optionally, cultures may further include one or more of: a retinoic acid (RA) antagonist, RA or RA agonist, bone morphogenic protein 7 (BMP7) and/or heparin. The respective concentrations and effects of retinoic acid (RA) antagonist, RA agonist, bone morphogenic protein 7 (BMP7); and/or heparin may be as hereinbefore described.

Inducing Vascularization

Suitably, at least partial vascularization and/or the presence of vascular progenitor cells in the renal organoids or aggregates is facilitated by conditions that promote or direct development of vascular endothelium or vascular progenitors from mesenchyme cells or tissues.

Suitably, aggregates of differentiated cells and/or organoids produced according to the aforementioned aspects may be cultured under conditions that facilitate at least partial vascularization, particularly vascularization of glomerular structures, or at least the production of progenitors of vascular endothelium or other vascular cells or tissues. In some embodiments, vascularization is facilitated by conditions that promote or direct development of vascular endothelium form mesenchyme cells or tissues.

In one embodiment, the method may include co-culturing vascular endothelial progenitors (such as differentiated from human pluripotent stem cells) together with IM cells as described above, or added to cultures of at least partly differentiated nephron progenitor cells and ureteric epithelial progenitor cells, to thereby produce vascular cells or tissues such as vascular endothelium.

In another embodiment, the method may include reduced oxygen tension during culture. Typically, 21% $O_2$ is the usual oxygen tension present in a standard tissue culture incubator. The invention contemplates to 5 to 12% $O_2$, which may be more equivalent to the oxygen tension experienced in the developing embryo. This may improve the capacity of the metanephric mesenchyme to generate VEGFA and thereby induce the formation and migration of Flk1$^+$ vascular endothelial progenitors.

In light of the foregoing, reference to protein agents such as BMP4, BMP7, Activin A, FGF2, FGF9 and FGF20 should be understood as encompassing native or recombinant or chemical synthetic proteins of any mammalian origin, inclusive of human, mouse and rat, although without limitation thereto. Furthermore, these proteins may include chemical modifications, glycosylation, lipidation, labels such as biotin and additional amino acid sequences such as epitope tags or fusion partners as are well known in the art. Typically, the aforementioned proteins may be obtained commercially and/or prepared as recombinant or chemical synthetic proteins by routine laboratory or manufacturing procedures.

In another aspect, the invention provides isolated or purified nephron progenitor cells, ureteric epithelial progenitor cells and/or renal organoids produced according to the methods disclosed herein.

Preferably, the renal organoid comprises segmented nephrons surrounded by endothelia and renal interstitium.

In a particular embodiment, the nephrons are segmented into four (4) or more components, including collecting duct (phenotypically GATA3$^+$ECAD$^+$), early distal tubule (phenotypically GATA3$^-$LTL$^-$ECAD$^+$), early proximal tubule (phenotypically LTL$^+$ECAD$^-$) and glomerulus (phenotypically WT1$^-$). Suitably, collecting duct trees are formed at the bottom of the organoid, connecting to distal and proximal tubules in the middle, with glomeruli at the top of the organoid.

It will be appreciated that nephron progenitor cells and/or ureteric epithelial progenitor cells may be obtained after an appropriate period of culture as hereinbefore described and in some optional embodiments may be further enriched or purified according to co-expression of surface markers. Cell enrichment or purification may be by any technique or process known in the art inclusive of flow cytometric cell sorting (e.g. FACS), positive or negative cell selection by magnetic immunobeads (e.g. Dynabeads™), panning, density separation, complement mediated lysis or the like, although without limitation thereto.

Kidney Regeneration and Transplantation

Chronic kidney disease is a serious medical condition that affects 31 million Americans and 1.7 million Australians each year. Patients can lose 90% of their kidney function before they become symptomatic. resulting in kidney failure and dialysis or a kidney transplant. Medicare expenditure in the U.S. for end-stage renal disease was estimated at $28 billion in 2010.

Accordingly, an aspect of the invention provides a method of producing a kidney, or kidney cells or tissues, said method including the step of differentiating the kidney, or the kidney cells or tissues from the isolated or purified nephron and/or ureteric epithelial progenitor cells to thereby produce the kidney, or kidney cells or tissues. Furthermore, this aspect of the invention provides at least partial vascularization and/or the generation of vascular progenitor cells under conditions that promote or direct development of vascular endothelium or vascular progenitors from mesenchyme cells or tissues.

The invention provides a method for producing cells of the ureteric epithelium and metanephric mesenchyme lineages or compartments. Preferably, these cells are simultaneously induced and direct the differentiation of each other in vivo. These cells are capable of developing into distinct tubular epithelial structures, including ureteric tree and nephron progenitor mesenchyme. It is therefore proposed that the hPSC cell-derived ureteric epithelium and/or nephron progenitor cells produced according to the invention may be directed to differentiate into renal cells from both the ureteric and mesenteric mesenchymal compartments. Under appropriate conditions, the nephron progenitor cells may be capable of differentiating into any nephron segment (other than collecting duct) including nephron epithelia such as connecting segment, distal convoluted tubule (DCT) cells, distal straight tubule (DST) cells, proximal straight tubule (PST) segments 1 and 2. PST cells, podocytes, glomerular endothelial cells, ascending loop of Henle and/or descending loop of Henle, although without limitation thereto.

Furthermore, the capacity of these cells to 'self-organise' may therefore be exploited to facilitate kidney repair, such as by way of kidney tissue or organ bioengineering.

It will be appreciated that one embodiment of the method of this aspect may include adoptively transferring or transplanting the isolated or purified nephron and/or ureteric epithelial progenitor cells into a human to thereby produce the kidney, or kidney cells or tissues.

According to this embodiment, differentiation of the isolated or purified nephron and/or ureteric epithelial progenitor cells into the kidney or kidney cells or tissues occurs in vivo Another embodiment of the method of this aspect may include at least partly differentiating the isolated or purified nephron and/or ureteric epithelial progenitor cells in vitro into kidney, or kidney cells or tissues, or progenitors of these. Suitably, the at least partly in vitro differentiated cells kidney, or kidney cells or tissues, or progenitors thereof, are adoptively transferred or transplanted into a human.

According to either or both embodiments, the kidney, kidney cells or tissues may facilitate or contribute to regeneration or repair of the kidney, cells or tissues thereof.

One embodiment provides use of an organoid, orisolated nephron progenitors and/or ureteric epithelial progenitors obtained therefrom, to produce an engineered or artificial kidney. For example, isolated nephron progenitors and/or ureteric epithelial progenitors may be incorporated within a scaffold, such as a decellularised human kidney or extracellular matrix (ECM) component thereof, polyester fleece or biodegradable polymer scaffold, to thereby produce a regenerated renal tubule structure. By way of example, such methods may include one or more of: (a) isolating one or more differentiated cell types and/or or intermediate progenitor cell types from the organoids; and (b) delivering the one or more differentiated cell types and/or or intermediate progenitor cell types into a decellularised kidney scaffold. In some embodiments the ECM from a kidney scaffold may be used as a matrix (e.g. generated from the ECM alone or in association with a hydrogel) in which to seed or bioprint the one or more differentiated cell types and/or or intermediate progenitor cell types to thereby recellularize the kidney scaffold or matrix.

Another embodiment may relate to repairing a damaged or diseased kidney. By way of example, the method may include one or more of (i) isolating one or more differentiated cell types and/or or intermediate progenitor cell types from the organoids: (ii) delivering the one or more differentiated cell types and/or or intermediate progenitor cell types into a damaged or diseased kidney to thereby facilitate repair and/or regeneration of the diseased or damaged kidney. Delivery might by directly into the damaged or diseased kidney via parenchymal injection or via a vascular route.

Another embodiment of the invention provides use of kidney cells or tissues differentiated from the isolated nephron progenitors and/or ureteric epithelial progenitors in devices for assisting or facilitating renal dialysis. For example, bioartificial kidneys may be made by seeding kidney cells, or their progenitors into reactors to produce a 'renal assistance device' for use in parallel with dialysis.

Also contemplated are "bioprinted" kidneys or other nephron-containing organs, organoids or organ-like structures using kidney cells or tissues differentiated or otherwise obtained from the isolated nephron progenitors and/or ureteric epithelial progenitors described herein.

Thus one particular aspect of the invention provides a method of bioprinting a renal structure, said method including depositing a plurality of hPSCs or other progenitor cells disclosed herein to form a renal structure having one or more functional characteristics of a kidney or component thereof, or which is capable of developing one or more functional characteristics of a kidney or component thereof.

Suitably, the hPSCs or other progenitor cells are subjected to a method disclosed herein for producing nephron progenitor cells and ureteric epithelial progenitor cells in the three-dimensional structure.

This particular aspect also provides a bioprinted renal structure having one or more functional characteristics of a kidney or component thereof, or which is capable of developing one or more functional characteristics of a kidney or component thereof, produced by the aforementioned method.

Another particular aspect of the invention provides a method of bioprinting a renal structure, said method including depositing a plurality of nephron progenitor cells and ureteric epithelial progenitor cells disclosed herein to form a renal structure having one or more functional characteristics of a kidney or component thereof, or which is capable of developing one or more functional characteristics of a kidney or component thereof.

Suitably, the nephron progenitor cells and ureteric epithelial progenitor cells have been produced from hPSCs by a method disclosed herein. In some embodiments, the method produces a bioprinted renal structure that has, or is capable of developing, at least partial vascularization and/or vascular progenitor cells.

This particular aspect also provides a bioprinted renal structure having one or more functional characteristics of a kidney or component thereof, or which is capable of developing one or more functional characteristics of a kidney or component thereof, produced by the aforementioned method. In some embodiments. the bioprinted renal structure that has, or is capable of developing, at least partial vascularization and/or vascular progenitor cells.

Suitably, the bioprinted renal structure is a three-dimensional renal structure.

It will also be appreciated that the three-dimensional structure may be constructed or formed from a plurality of bioprinted "layers" or "arrays", as will be described in more detail hereinafter.

The bioprinted renal structure component may be, or comprise, any structural and/or functional component of a kidney, such as a glomerulus, juxtaglomerular apparatus, interstitial tissue, collecting ducts, Bowman's capsule, proximal and/or distal convoluted tubules, vasculature such as arterioles, arteries, veins and/or capillaries, although without limitation thereto.

Suitably, the bioprinted renal structure is at least partly vascularized and/or comprises vascular progenitor cells.

In some embodiments, the bioprinted kidney or kidney component may be implantable or otherwise adoptively transferable into a host.

As used herein, "bioprinting" includes and encompasses utilizing three-dimensional, precise deposition of cells (e.g., cell solutions, cell-containing gels, cell suspensions, cell concentrations, multicellular aggregates. organoids, multicellular bodies, etc.) via methodology that is compatible with an automated or semi-automated, computer-aided, three-dimensional prototyping device (e.g., a bioprinter). In this regard, reference is made to United States Patent Applications US20120116568. US20130164339 and US20140012407 which are herein incorporated by reference and provide non-limiting examples of potentially suitable bioprinting techniques.

By way of example, in some embodiments, at least one component of an engineered, implantable renal organoid tissue and/or organ may bioprinted. In further embodiments, the engineered, implantable tissues and/or organs are entirely bioprinted. In still further embodiments, bioprinted constructs are made with a method that utilizes a rapid prototyping technology based on three-dimensional, automated, computer-aided deposition of renal cells as disclosed herein, including cell solutions, cell suspensions, cell-comprising gels or pastes, cell concentrations, multicellular bodies (e.g., cylinders, spheroids, ribbons. etc.), and confinement material onto a biocompatible surface (e.g., composed of hydrogel and/or a porous membrane) by a three-dimensional delivery device (e.g., a bioprinter). As used herein, in some embodiments, the term "engineered," refer to renal tissues and/or organs means that cells, cell solutions, cell suspensions, cell-comprising gels or pastes, cell concentrates, multicellular aggregates, and layers thereof are positioned to form three-dimensional structures by a computer-aided device (e.g., a bioprinter) according to a computer script. In further embodiments, the computer script is, for example, one or more computer programs, computer applications, or computer modules. In still further embodiments, three-dimensional tissue structures form through the post-printing fusion of cells or multicellular bodies similar to self-assembly phenomena in early morphogenesis.

While a number of methods are available to arrange cells, multicellular aggregates, and/or layers thereof on a biocompatible surface to produce a three-dimensional structure including manual placement, positioning by an automated, computer-aided machine such as a bioprinter is advantageous. Advantages of delivery of cells or multicellular bodies with this technology include rapid, accurate, and reproducible placement of cells or multicellular bodies to produce constructs exhibiting planned or pre-determined orientations or patterns of cells, multicellular aggregates and/or layers thereof with various compositions. Advantages also include assured high cell density, while minimizing cell damage. In some embodiments, the method of bioprinting is continuous and/or substantially continuous. A non-limiting example of a continuous bioprinting method is to dispense bio-ink from a bioprinter via a dispense tip (e.g., a syringe, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries. In further embodiments, a repeating pattern of bioprinted function units comprises a layer or array and a plurality of layers or arrays are bioprinted adjacently (e.g., stacked) to form an engineered tissue or organ. In various embodiments, 2, 3, 4, 5, 6, 7, 8, 9, 10, 11, 12, 13, 14, 15, or more layers or arrays are bioprinted adjacently (e.g., stacked) to form an engineered renal tissue or organ.

In some embodiments, a bioprinted functional unit repeats in a tessellated pattern. A "tessellated pattern" is a plane of figures that fills the plane with no overlaps and no gaps. Advantages of continuous and/or tessellated bioprinting include, by way of non-limiting example, increased productivity of bioprinted tissue. Another non-limiting, exemplary advantage is eliminating the need to align the bioprinter with previously deposited elements of bio-ink. Continuous bioprinting also facilitates printing larger tissues from a large reservoir of bio-ink optionally using a syringe mechanism.

In various embodiments, methods for continuous bioprinting involve optimizing and/or balancing parameters such as print height, pump speed, robot speed. or combinations thereof independently or relative to each other. In one example, the bioprinter head speed for deposition was 3 mm/s, with a dispense height of 0.5 mm for the first layer and dispense height was increased 0.4 mm for each subsequent layer. In some embodiments, the dispense height is approximately equal to the diameter of the bioprinter dispense tip. Without limitation a suitable and/or optimal dispense distance does not result in material flattening or adhering to the dispensing needle. In various embodiments, the bioprinter dispense tip has an inner diameter of about, 20, 50, 100, 150, 200, 250, 300, 350, 400, 450, 500, 550, 600, 650, 700, 750, 800, 850, 900, 950, 1000 μm, or more, including increments therein. In various embodiments, the bio-ink reservoir of the bioprinter has a volume of about 0.5, 1, 2, 3, 4, 5, 6, 7, 8, 9, 10, 15, 20, 25, 30, 35, 40, 45, 50, 55, 60, 65, 70, 75, 80, 85, 90, 95, 100 $cm^3$, or more, including increments therein. In some embodiments, the pump speed is suitable and/or optimal when the residual pressure build-up in the system is low. In some embodiments, favourable pump speeds depend on the ratio between the cross-sectional areas of the reservoir and dispense needle with larger ratios requiring lower pump speeds. In some embodiments, a suitable and/or optimal print speed enables the deposition of a uniform line without affecting the mechanical integrity of the material.

By way of example only, Organovo partnered with Invetech have developed an organ printing machine which uses a hydrogel scaffold to place human cells in a desired orientation to recreate human organs. Kidney cells or tissues differentiated or otherwise obtained from the isolated nephron progenitors and/or ureteric epithelial progenitors described herein may be used with machines, such as the Organovo machine referred to above, to develop a "bioprinted" human kidney organoid or kidney.

Another aspect of the invention provides an array of nephron progenitors and ureteric progenitors having a planar geometry.

The array may comprise a plurality of stacked arrays, preferably 2, 3, 4, 5, 6, 7, 8, 9, 10, 11, 12, 13, 14 or 15 or more stacked arrays.

The arrays may stacked in a tessellated pattern.

A related aspect of the invention provides kidney organoid obtained by maturing the array of the aforementioned aspect Suitably, the renal organoids are at least partially vascularized and/or comprise vascular progenitors.

It will also be appreciated that the directed differentiation of isolated nephron progenitors and/or ureteric epithelial progenitors, organoids and bioprinted renal structures described herein may be potential sources of purified, differentiated renal cell subtypes, organoids and/or bioprinted renal structures for cellular therapy.

For example, the isolated nephron progenitors and/or ureteric epithelial progenitors described herein may be useful for generating renal cells or tissues after gene correction in certain genetically-inherited renal conditions. For example, correction of single gene renal disorders, including Alport syndrome (COL4A3 mutation) and the polycystic kidney diseases (PKD1, PKD2 and others), may be assisted or facilitated by regeneration of renal tissue from the isolated nephron progenitors and/or ureteric epithelial progenitors described herein after gene correction.

In a particular embodiment, iPSC lines derived, obtained or originating from a patient with genetic renal disease may be used for repair of genetic mutation(s) in vitro. Such cells could be used according to the method of the invention and then administered to the patent for autologous cellular therapy.

Nephrotoxicity Screening

It will also be appreciated that the directed differentiation of isolated nephron progenitors and/or ureteric epithelial progenitors described herein may provide potential sources of purified, differentiated renal cells, bioprinted renal structures, renal organoids, arrays or renal tissue subtypes for nephrotoxicity screening.

The development of interventions aimed at preventing disease, including drug and cellular-based therapies, is made difficult by the lack of availability of primary human kidney cells for in vitro drug testing.

Accordingly, another aspect of the invention provides a method of determining the nephrotoxicity of one or a plurality of compounds. said method including the step of contacting the one or plurality of compounds with the nephron progenitor cells and/or ureteric epithelial progenitor cells described herein, either as an organoid or after isolation and purification, or kidney cells or tissues differentiated or otherwise obtained therefrom, to thereby determine whether or not the one or plurality of compounds is nephrotoxic.

Preferably, the method is performed using organoids or from isolated or purified nephron progenitor cells, or kidney cells or tissues derived from the nephron progenitor cells.

Many useful drugs have nephrotoxic side effects, such as by direct tubular effects (e.g. aminoglycoside antibiotics, cisplatin, radiocontrast media, NSAIDs, ACE inhibitors), interstitial nephritis (e.g. β lactam antibiotics, lithium, CsA, anti-epileptic drugs such as phenytoin) or glomerulonephritis, for example. It may therefore be advantageous to test new or existing drugs using defined, specific kidney cells and tissue types differentiated or otherwise obtained from the isolated or purified nephron progenitor cells described herein. The hereinbefore described "bioprinted" kidney or bioprinted kidney organoid may also be applicable to nephrotoxicity screening.

Nephrotoxicity may be assessed or measured by any appropriate test for renal cell function in vitro, including decreased creatinine clearance or biomarker expression such as by the Human Nephrotoxicity $RT^2$ Profiler™ PCR Array from Qiagen or the High Content Analysis (HCA) Multiplexed Nephrotoxicity Assay from Eurofins, although without limitation thereto.

As described in more detail in the Examples, cisplatin is a nephrotoxicant that induces caspase-mediated acute apoptosis of proximal tubular cells in the kidney cisplatin treatment of renal organoids induced specific acute apoptosis in mature proximal tubular cells, whereas immature cells did not undergo apoptosis.

So that the invention may be readily understood and put into practical effect, reference is made to the following non-limiting Examples.

EXAMPLES

Work leading to the present invention identified specific in vitro culture conditions that are tailored to promote the synchronous, simultaneous differentiation of nephron progenitor cells and ureteric epithelial progenitor from intermediate mesoderm (IM). More specifically, FGF9 plus heparin alone, or in combination with one or more agents including bone morphogenic protein 7 (BMP7), retinoic acid (RA), an RA antagonist; a Wnt agonist; and/or FGF20 plus heparin, is capable of facilitating differentiation of intermediate mesoderm into nephron progenitor cells and ureteric epithelial progenitors. Further to this, the in vitro culture method provides a system for differentiating hPSCs through posterior primitive streak, IM and metanephric mesenchymal stages to produce nephron progenitor cells and ureteric epithelial progenitor cells. The presence or absence of certain molecules such as RA, RA antagonist and/or Wnt agonist could be manipulated to preferentially promote the production of nephron progenitor cells versus ureteric epithelial progenitors, or vice versa. The posterior PS is the progenitor population for the mesoderm such as the IM, and is induced from hPSCs using a Wnt agonist (e.g. CH1R99021). The IM differentiates to two key kidney progenitor populations: the ureteric epithelium (UE), the progenitor of collecting ducts; the metanehpric mesenchyme (MM), the progenitor of nephrons. While the anterior IM gives rise to UE, the posterior IM develops to the MM. Here, we present a method to induce both the anterior and posterior IM at the same time by the carefully determined period of using CHIR99021. This simultaneous induction leads the successful generation of kidney organoids containing all anticipated renal components including nephrons, interstitia and endothelia. We also propose that the addition of an inhibitor of RA signalling, such as the synthetic potent pan-retinoic acid receptor (RAR) antagonist AGN 193109, would promote metanephric mesenchyme formation.

Example 1

Materials and Methods Non-limiting examples of sources of reagents referred to in these methods are provided in Table 1.
  Media are as follows:
  Gelatin solution: 0.1% gelatin in PBS. Then the solution is autoclaved.
  FDMEM: 89% DMEM high glucose. 10% Foetal Bovine Serum, 1% GlutaMAX Supplement, 0.5% Penicillin/Streptomycin.
  KSR medium: 77.8% DMEM/F-12, 20% Knockout Serum Replacement, 1% NEAA, 1% GlutaMAX, 0.5% Penicillin/Streptomycin, 0.2% 2-Mercaptoethanol (55 mM). Then medium is filtered by Stericup-GP.
  MEF-conditioned KSR medium: Feed 40 mL of KSR medium to 10 million Mouse embryonic fibroblast cells in T175 flask for a day. Collect the medium next day and feed another 40 mL of KSR medium. After repeating this 6 times, collected and pooled medium is filtered by Stericup-GP.
  APEL: Supplement a bottle of STEMdiff APEL (100 mL) with 0.5 mL of Antibiotic-Antimycotic.
  Reference is also made to International Publication WO2014/197934 and Takasato, M. et al., 2014, *Nat. Cell Biol.* 16, 118-26 for additional reagents, methods, PCR primers and the like, the entirety of which documents are incorporated herein by reference.
Seed Feeders (Day −8)
  Coat a 25 cm$^2$ tissue culture flask with 3 mL of 0.1% gelatin solution.
  Thaw frozen vial of mitotically inactivated mouse embryonic fibroblasts (MEFs) by warming vial at 37° C. until a small ice pellet remains. Add warmed 5 mL FDMEM media in a drop wise manner to vial and gently mix. Collect into 15 mL tube and centrifuge at 1,500 rpm for 3 minutes.
  Remove supernatant and resuspend MEFs in FDMEM. Seed onto flask at 12,000 cells per cm$^2$ in FDMEM and incubate overnight in a 37° C. $CO_2$ incubator.
Thaw hESC/iPSC (Day −7)
  Thaw frozen vial of iPSC/hESC onto the prepared 25 cm$^2$ tissue culture flask containing mitotically inactivated MEFs by warming vial at 37° C. until a small ice pellet remains. Add warmed 5 mL KSR media (see appendix A) in drop wise manner to vial and gently mix. Collect into 15 mL tube and centrifuge at 1,500 rpm for 3 minutes.
  Prepare 5 mL KSR media per 25 cm$^2$ tissue culture flask. Add 10 ng/mL bFGF to KSR media.
  Remove supernatant and resuspend iPSC/hESC in KSR media containing 10 ng/mL bFGF. Seed onto flask and incubate in a 37° C. $CO_2$ incubator for 3 days.
  Daily, aspirate spent KSR media and replenish with 5 mL fresh KSR media containing 10 ng/mL bFGF.
Dissociating and Matrigel Adaption of hESC/iPSC (Day −3)
Matrigel Coating:
  Aliquot 3 mL of cold DMEM/F12 basal media into a 15 mL tube.
  Add 25 uL of hESC qualified Matrigel to DMEM/F12. Mix well and transfer into a 25 cm$^2$ tissue culture flask. (*handle Matrigel on ice as it solidifies when warmed.)
  Keep flask at room temperature for at least 30 minutes to allow Matrigel to coat the surface.
  Prepare 5 mL MEF conditioned KSR media (see appendix B) and add 10 ng/mL bFGF to media.
Dissociating Cells:
  (*For optimal results. cells should be approximately 80-90% confluent. If cells are not confluent, allow another day for incubation or do a lower split ratio.)
  Wash confluent 25 cm$^2$ flask with 3 mL PBS twice.
  Add 2 mL TrypLE Select to cells and incubate at 37° C. for 3 minutes.
  Pipette 5 mL DMEM/F12 basal media to cells, mix and ensure cells have lifted off from the plastic surface.
  Collect cell suspension at a 1:3 split ratio in a 15 mL tube and centrifuge at 1,500 rpm for 3 minutes.
Seeding Cells onto Matrigel Coated Flasks:
  Remove supernatant and add prepared 5 mL conditioned KSR media to cells. Mix gently.
  Aspirate Matrigel-containing DMEM/F12 from prepared tissue culture flask and seed cells.
  Incubate overnight in a 37° C. $CO_2$ incubator for two days.
  Daily, aspirate spent conditioned KSR media and replenish with 5 mL fresh conditioned KSR media containing 10 ng/mL bFGF.
Seeding Cells for Differentiation (Day −1)
  Wash 25 cm$^2$ flask with 3 mL PBS twice.
  Add 2 mL TrypLE Select to cells and incubate at 37° C. for 3 minutes.
  Pipette 5 mL DMEM/F12 basal media to cells, mix and ensure cells have lifted off from the plastic surface.
  Collect cell suspension into 15 mL tube. Count.
  Calculate desired cell numbers to achieve 4,000 cells per well (12,500 cells per cm$^2$).
  Aliquot desired cell numbers into a 15 mL tube. Centrifuge at 1,500 rpm for 3 minutes.
  Resuspend cells in conditioned KSR, containing 10 ng/mL bFGF, at 50 uL per well. Seed cells into 96 well glass bottom plate and incubate at 37° C. overnight.
Differentiation Stage One (Day 0)
  For a freshly opened APEL bottle, add Antibiotic-Antimycotic (100×) at 1 in 100.
  Prepare 8 μM CHIR in APEL.
  Aspirate conditioned KSR from 96 well plate.
  Add 100 μL of APEL containing 8 μM CHIR to cells.
  Incubate at 37° C. for 4 days, refreshing the media every 2 days.
Differentiation Stage Two (Day 4)
  Prepare 200 ng/mL FGF9+1 μg/mL Heparin in APEL.
  Aspirate spent APEL containing CHIR from 96 well plate.

Add 100 µL of APEL containing 200 ng/mL FGF9+1 µg/mL Heparin to cells.

Incubate at 37° C. for 2 days, and refreshing the media on day 6 with fresh APEL containing 200 ng/mL FGF9+1 g/mL Heparin.

3D Organoid Culture (Day 7)

Obtain cultured C32 IPS cells of different conditions in 96 well plate.

Aspirate the culturing media and give a quick wash with sterile PBS.

Aspirate the PBS.

Add 50 µL of trypsin EDTA (0.25%) to each well.

Place in 37° C. incubator for up to 3 minutes for cells to lift off the surfaces.

Monitor under the microscope to make sure all cells have lift off the glass (96 well) surfaces. If the cells are still attached to the surfaces, gently pipette the cells with trypsin and place back into the incubator for further 2 minutes.

Neutralize the trypsin with 100 µL of DMEM+10% FBS+1% P/S.

Aliquot the entire culture into a 15 mL Falcon tube.

Centrifuge the cells at a speed of 1500 rpm for 5 mins.

Aspirate the media off till just a pellet of cells left.

Resuspend the cells with 3 mL of CHIR.

Take out 10 µL of cell suspension and perform a cell count with a haemocytometer.

Each 3D pellet organoid will have roughly $5 \times 10^5$ cells, aliquot the required amount of cell suspension into a 15 mL Falcon tube.

Centrifuge the tube at 2000RPM for 2 minutes.

Aliquot 1.2 mL of APEL+5 µM CHIR into the 6 well Transwell polyester membrane cell culture plate.

Use a P1000 pipette to slowly dislodge the pellet in solution with APEL.

Pick the pellet up by using a P1000 wide bore tips.

Carefully plate the pellet onto the transwell filters with minimal media carry over.

Placed in a cell culture incubator for 1 hr.

Aliquot 1.2 mL of APEL+200 ng/mL FGF9+1 µg/mL Heparin into a Corning Costar 6 well plate.

Remove the filters culturing for an hour in APEL+5 µM CHIR to the APEL+200 ng/mL FGF9+1 µg/mL Heparin plates and culture for 5 days. (Media change every two days)

After 5 days. remove the filters and place in a freshly prepared Corning Costar 6 well plate with 1.2 ml of fresh APEL.

Culture the organoids for further 6 days in APEL only media. (Media change every two days)

3D Organoid Immunofluorescence (Day 18)

After 6 days of organoid culture, fix the pellets with 1% paraformaldehyde at 4° C. for 20 minutes.

Remove the paraformaldehyde and wash three times with PBS.

Once fixed and washed, organoids can be stored at 4° C. for up to a week before immunofluorescence staining.

Aliquot around 150 uL of blocking buffer (10% donkey serum/0.3% Triton-x/PBS) into the MatTek Glass Bottom Dishes.

Carefully cut the organoids off the filter and submerge the filter into the blocking buffer.

Block the organoids for 2-3 hours.

Prepare primary antibodies of choice in blocking buffer. Most of the antibodies listed use a dilution of 1:300.

Aspirate the blocking buffer off the MatTek dish, and aliquot 150 µL of blocking buffer+primary antibodies into the MatTek dish.

Incubate the organoids with primary antibodies at 4° C. over-night.

Aspirate the primary antibodies off the dish and wash with PBTX for 6 times, 10 minutes each.

Prepare secondary antibodies (1:400 diln) of choice in PBTX (0.1% Triton-X/PBS).

Incubate organoids in secondary antibodies for 4 hours.

Remove secondary antibodies and incubate with DAPI (1:1000 diln) in PBS for 1 hour.

Wash 3 times, 10 minutes each with PBS.

Ready for imaging.

Results

Figure 1:
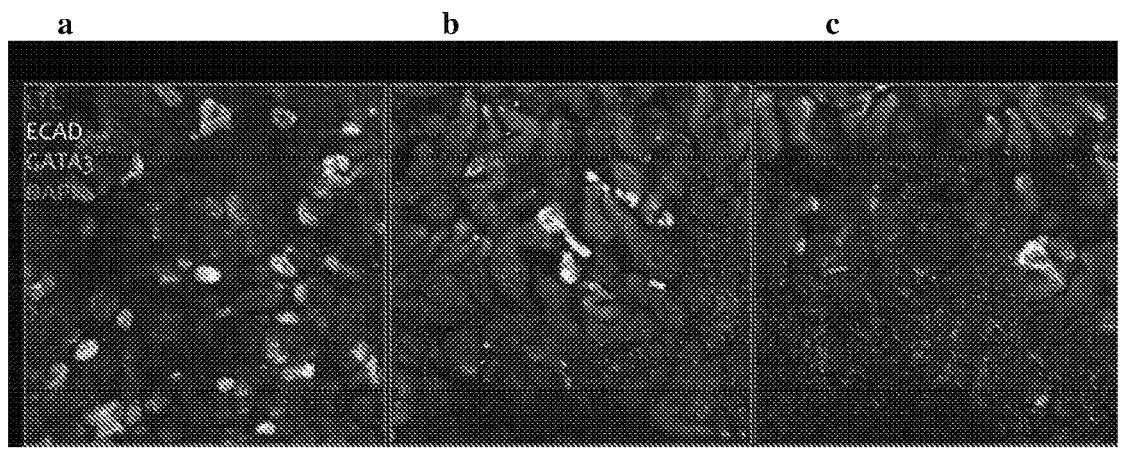
FIG. 1. Differential effects of culturing with CHIR for 3, 4 or 5 days followed by FGF9 alone (b) or together with RA (a) or an RA antagonist (c).

As shown in FIG. 1, to select for collecting duct (ECAD$^+$, GATA3$^+$, PAX2$^+$), fewer days (2-3) of initial Wnt agonist and/or subsequent culture with FGF9 together with activation of retinoic acid signalling is optimal. To select for nephron-forming metanephric mesenchyme (WT1$^+$ HOXD11$^+$ECAD$^-$) and giving rise to epithelial structures expressing early nephron markers), more days (3-5) of initial Wnt agonist and/or subsequent culture with FGF9 together with inhibition of retinoic acid signalling is optimal.

Figure 2:
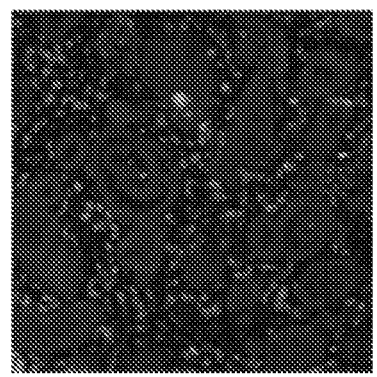
FIG. 2. Presence of a MEIS1$^+$ stromal population present between the forming nephrons. Red=MEIS1: Blue=nuclei.
Figure 3:
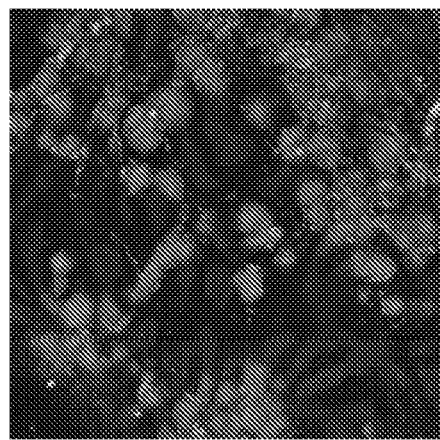
FIG. 3. Presence of CD31$^+$ vascular progenitors. Red=NPHS1 (podocyte), Blue=nuclei, Green=CD31.
Figure 4:
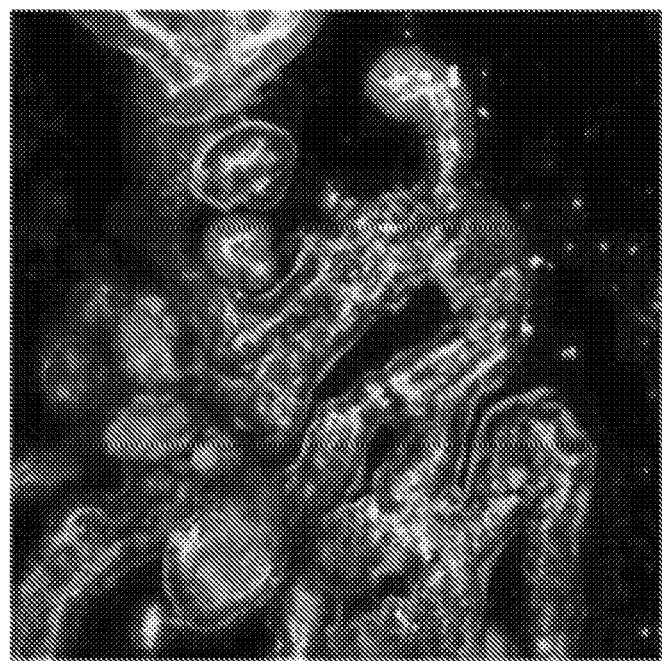
FIG. 4. Presence of all segments of a normal developing nephron, including collecting duct (GATA3$^+$PAX2$^+$ECAD$^+$), distal tubule (ECAD$^+$GATA3$^-$LTL$^-$), proximal tubule (LTL$^+$AQP1$^+$) and glomerulus (WT1$^+$NPHS1$^+$SYNPO$^+$), connected to each other suggestive of normal embryonic organogenesis. Pink=GATA3, Green=ECAD, Blue=LTL, Red=WT1, Collecting duct (Pink and green). Distal tubule (green), Proximal tubule (blue), glomeruli (red in nuclei).
Figure 5:
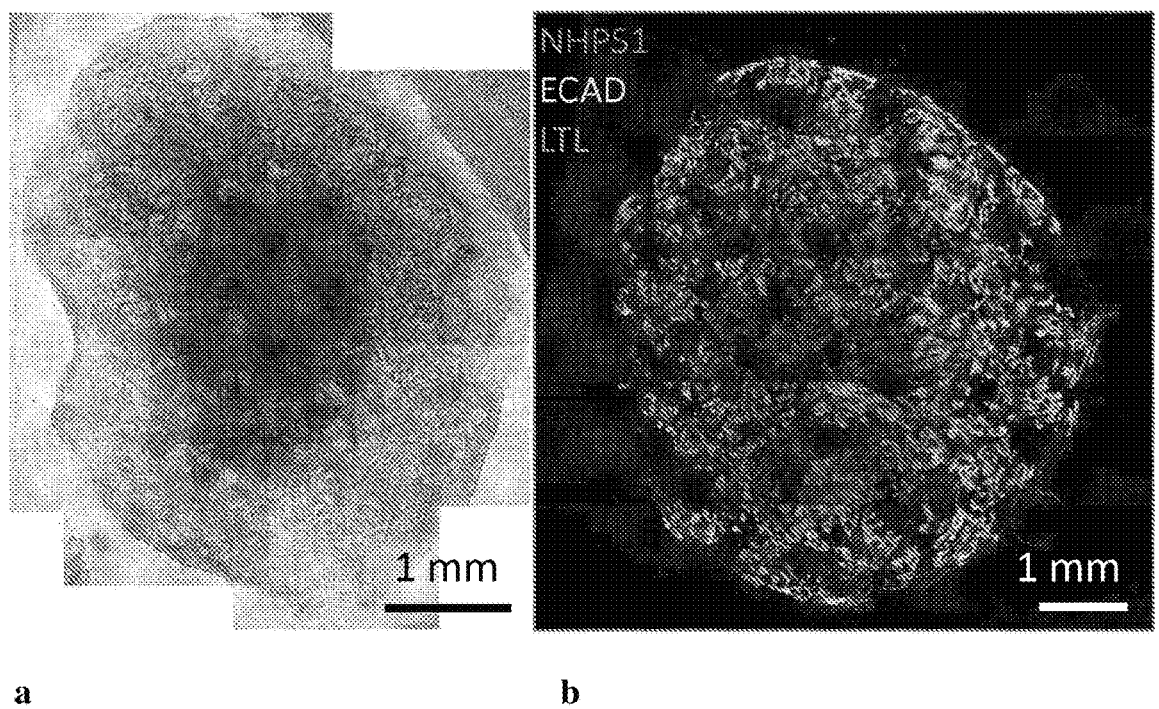
FIG. 5. Renal organoids of 11 days culture after being pelleted. a=an image of bright field showing 3 to 5 cm in diameter. b=an image of immunofluorescent staining. Green=ECAD, Red=NPHS1, Blue=LTL, Distal tubule (green), Proximal tubule (blue), glomeruli (red).

We now have evidence that organoids formed via the aggregation of human pluripotent stem cells using the method disclosed herein show the following features indicative of normal kidney organogenesis. As shown in FIG. 2, the presence of a Meis1$^+$ stromal population is shown to be present between the forming nephrons. This population is known to arise from metanephric mesenchyme, is present between the developing nephrons of the embryonic kidney and have been shown to contribute to the formation of the perivasculature of the final organ. In FIG. 3 the presence of CD31$^+$ vascular progenitors. We see evidence in endothelium as assessed by CD31, however CD31 is a marker of mature endothelium and as yet we do not see early endothelial progenitors showing active invasion of the glomeruli to form a functional filtration unit. FIGS. 4 and 5 show the presence of all segments of a normal developing nephron, including collecting duct (GATA3$^+$PAX2$^+$ECAD$^+$), distal tubule (ECAD$^+$GATA3$^-$LTL$^-$), proximal tubule (LTL$^+$ AQP1$^+$) and glomerulus (WT1$^+$NPHS1$^+$SYNPO$^+$), connected to each other suggestive of normal embryonic organogenesis.

Variations in a number of parameters has improved the overall size, complexity, maturity and nephron number present within organoids formed from human pluripotent stem cells.

Figure 6:
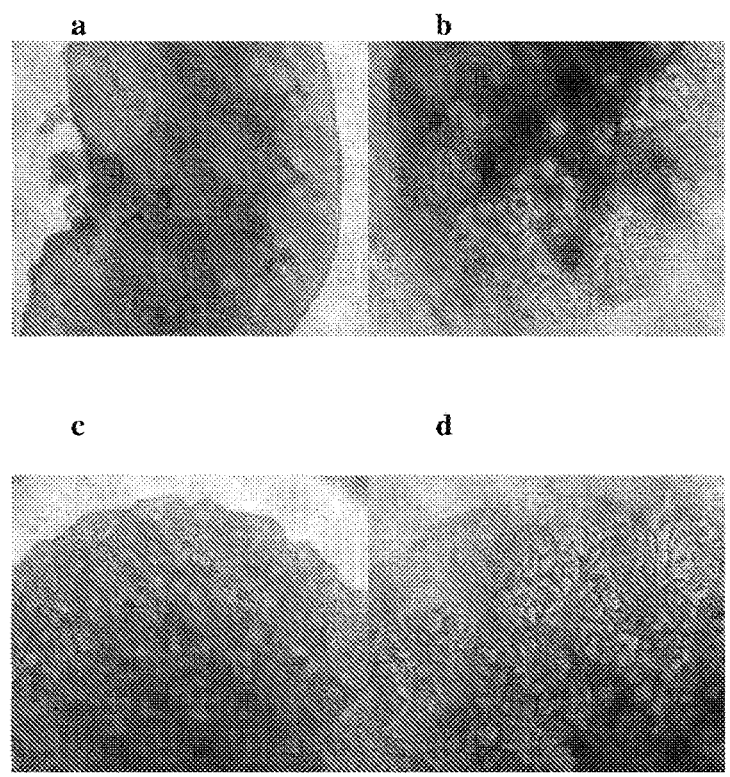
FIG. 6. Addition of a 45 minute pulse of high CHIR (5 μM) immediately upon reaggregation followed by culture in FGF9 with or without AGN (retinoic inhibitor), BMP7, low CHIR or RA for 5 days then without these factors for 6 days. a=4 day pellet with no CHIR: b=4 day pellet with 45 min CHIR pulse; c=11 day pellet with no CHIR: d=11 day pellet with 45 min CHIR pulse.

These include formation of an aggregate of differentiated cells for culture as an organoid after 7 days of induction. Initially, these were shown to be able to form after 14 or 18 days of prior culture. We can now reliably get organoid formation after 7 days with this including 4 days of culture in 8 µM CHIR followed by 3 days of culture in FGF9 with or without AGN (retinoic inhibitor), BMP7, low CHIR or RA in the concentration ranges previously described. As shown in FIG. 6, formation of aggregates was enhanced by addition of a 45 minute pulse of high CHIR (5 µM) immediately upon reaggregation followed by culture in FGF9 with or without AGN (retinoic inhibitor), BMP7. low CHIR or RA in the concentration ranges previously described.

The formation of a vascularised glomerulus is critical for renal function. Evidence that such glomerular vasculature can form even in vitro would significantly enhance the credibility of organoids as a model for the kidney.

One approach combines human pluripotent stem cells differentiated to kidney together with human pluripotent stem cells differentiated to vascular endothelial progenitors using a protocol such as that of Orlova[31].

Another approach reduces the oxygen tension during differentiation from 21% $O_2$ (usual oxygen tension present in a standard tissue culture incubator) to 5 to 12% $O_2$ (more equivalent to the oxygen tension experienced in the developing embryo). We anticipate that this may well improve the capacity of the metanephric mesenchyme to generate VEGFA and induce the formation and migration of Flk1+ endothelial progenitors.

Example 2

Cell Culture and Differentiation

All experiments presented used the previously described wildtype human iPSC line CRL1502 (clone#C32) generated using episomal reprogramming[28]. Undifferentiated human iPSCs were maintained on the mouse embryonic fibroblasts (MEFs) (Millipore) as a feeder layer with human ES cell (hES) medium as described previously[1]. Cells were authenticated and tested for the *mycoplasma* infection[28]. Human iPSCs were plated on a Matrigel-coated (Millipore) culture dish and cultured in MEF-conditioned hES medium (MEF-CM) until reaching to 60-100% confluent. Then, cells were again plated on a Matrigel-coated at 5,000 cells/cm$^2$ in MEF-CM. Next day, cells reached to 40-50% of confluent, cells were treated with 8 µM of CHIR99021 in APEL basal medium (STEMCELL Technologies) supplemented with Antibiotic-Antimycotic (Life Technologies) for 2-5 days, followed by FGF9 (200 ng mL$^{-1}$) and Heparin (1 µg mL$^{-1}$) for another 5-2 days, with changing medium every second day. At day 7, cells were collected and dissociated into single cells using Trypsin or TrypLE select (Life Technologies). Cells (0.5×10$^6$) were spun down at ×400 g for 2 min to form a pellet and then transferred onto a Transwell 0.4 µm pore polyester membrane (#CLS3450 Corning). Pellets were treated with 5 µM of CHIR99021 in APEL for 1 h, and then cultured with FGF9 (200 ng mL$^{-1}$) and Heparin (1 µg mL$^{-1}$) for 5 days, followed by another 6-13 days in APEL basal medium, with changing medium three times a week. Culture medium should not exceed above a membrane. For the differentiation in monolayer cultures, cells post CHIR99021 induction were treated by FGF9 (200 ng mL$^{-1}$) and Heparin (1 µg mL$^{-1}$) for 10 days, followed by APEL basal medium for another 6 days. In some experiments, RA (0.1 µM) or AGN193109 (5 µM) were added to FGF9 medium. A step-by step protocol describing kidney organoid generation was provided in Example 1.

Immunocytochemistry

For monolayer cells, antibody staining was performed as described previously[1]. For the kidney organoid, organoids were fixed with 2% paraformaldehyde in PBS for 20 min at 4° C. followed by 3 times wash with PBS. Then organoids were blocked with 10% donkey serum, 0.3% Triton X/PBS for 2-3 h at room temperature and incubated with primary antibodies overnight at 4° C. After 5 times washing with 0.1% Triton X/PBS. secondary antibodies were incubated for 4 h at room temperature. The following antibodies and dilutions were used: rabbit anti-PAX2 (1:300, #71-6,000, Zymed Laboratories), goat anti-SIX1 (1:300, #sc-9709, Santa Cruz Biotechnology), rabbit anti-SIX2 (1:300, #11562-1-AP, Proteintech), mouse anti-ECAD (1:300, #610181. BD Biosciences), rabbit anti-WT1 (1:100, #sc-192, Santa Cruz Biotechnology), mouse anti-HOXD11 (1:300, #SAB1403944, Sigma-Aldrich), goat anti-GATA3 (1:300, AF2605, R&D Systems). rabbit anti-JAG1 (1:300, #ab7771, Abcam), goat anti-Cubilin (1:150, #sc-20607. Santa Cruz Biotechnology), sheep anti-NPHS1 (1:300, AF4269, R&D Systems), LTL-biotin-conjugated (1:300, B-1325, Vector Laboratories), DBA-biotin-conjugated (1:300, B-1035, Vector Laboratories), mouse anti-KRT8 (1:300, #TROMA, DSHB), mouse anti-CD31 (1:300, #555444, BD Pharmingen), rabbit anti-KDR (1:300, #2479, Cell Signaling Technology), goat anti-SOX17 (1:300, #AF1924, R&D Systems), rabbit anti-NG2 (1:300, #AB5320, Merck Millipore), rabbit anti-SMA (1:300, #ab15267. Abcam), mouse anti-PDGFRA (1:200, #556001. BD Pharmingen), rabbit anti-Laminin (1:300, #L9393, Sigma-Aldrich), rabbit anti-UMOD (1:300, #BT-590, Biomedical Technologies), mouse anti-MEIS1 (1:300, #ATM39795, activemotif), goat anti-FOXD1 (1:200, #sc-47585, Santa Cruz Biotechnology) and rabbit anti-cleaved-CASP3 (1:300, #9661, Cell Signaling Technology). Images were taken using a Nikon Ti-U microscope or a Zeiss LSM 780 confocal microscope. All immunofluorescence analyses were successfully repeated more than three times and representative images are shown.

Electron Microscopy

Organoids were processed for electron microscopy using a method as follows. A solution of 5% glutaraldehyde in 2×PBS was added directly to the organoid culture dish in equal volume to the growth medium and placed under vacuum for 5 min. The organoid was reduced in size by cutting into small blocks (~2×2 mm), and irradiated in fresh fixative 2.5%, again under vacuum, for 6 minutes, in a Pelco Biowave (Ted Pella In, Redding, Calif.) at 80 W power. Samples were then washed 4×2 min in 0.1 M cacodylate buffer. Samples were then immersed in a solution containing potassium ferricyanide (3%) and osmium tetroxide (2%) in 0.1M cacodylate buffer for 30 min at room temperature. Following 6×3 min washes in distilled water the tissue blocks were then incubated in a filtered solution containing thiocarbohydrazide (1%) for 30 min at room temperature. After subsequent washing in distilled water (6×2 min) samples were incubated in an aqueous solution of osmium tetroxide (2%) for 30 min, then in distilled water (6×2 min) and incubated in 1% aqueous uranyl acetate for 30 min at 4° C. After further distilled water washes (2×2 min) a freshly prepared filtered solution of 0.06% lead nitrate in aspartic acid (pH 5.5) warmed to 60° C. was added to the dish and further incubated for 20 minutes at 60° C. before rinsing in distilled water (6×3 min) at room temperature. Tissue blocks were dehydrated twice in each ethanol solution of 30%, 50%, 70%, 90% and absolute ethanol for 40 sec at 250 watt in the Pelco Biowave. Epon LX112 resin was used for embedding the tissue with infiltration at 25%, 50%, and 75% resin:absolute ethanol in the Pelco Biowave under vacuum at 250 watt for 3 min and finishing with 100% resin (twice), before the final embedding/blocking and curing at 60° C. for 12 hours.

qRT-PCR Analysis

Total RNA was extracted from cells using Purelink RNA mini kit (Life Technologies) and cDNA was synthesized from >100 ng total RNA using Super Script III reverse transcriptase (Life Technologies). qRT-PCR analyses were performed with GoTaq qPCR Master Mix (Promega) by Roche LightCycler 96 real-time PCR machine. All absolute data were first normalized to GAPDH and then normalized to control samples (δ-δ-Ct method). The sequences of primers used for qRT-PCR are as listed in Table 2.

Next Generation RNA Sequencing and Comparative Analysis Using KeyGenes

Sequencing was performed using the Illumina NextSeq500 (NextSeq control software v1.2/Real Time Analysis v2.1) platform. The library pool was diluted and denatured according to the standard NextSeq500 protocol and sequencing was carried out to generate single-end 76 bp reads using a 75 cycle NextSeq500 High Output reagent Kit (Catalog #FC-404-1005). Reads were mapped against the reference human genome (hg19) using STAR[29], and read counts for each gene in the UCSC annotation were generated using htseq-count in the HTSeq python package (http://www-huber.embl.de/users/anders/HTSeq/doc/index.htm). The number of uniquely mapped reads ranged from 18810634-36706805 per sample. Normalised read counts were calculated using the DESeq2 package[30].

KeyGenes has used to generate the identity scores of D0, D3, D11, D18 kidney organoids to different first trimester human organs, including the kidneys (GSE66302)[15]. A dendrogram (FIG. 13) showing the hierarchical clustering of D0, D3, D11, D18 kidney organoids and 21 human fetal organs from first and second trimester (GSE66302) was based on the Pearson correlation of the expression levels of 85 classifier genes as determined by KeyGenes (www.keygenes.nl; Table 3). The classifier genes were calculated by KeyGenes using the top 500 most differentially expressed genes of the human fetal data without including the extra-embryonic tissues from that data set.

Functional Analysis for Proximal Tubules

For Dextran uptake assay, organoids at day 17 were cultured with 10 µg mL$^{-1}$ of 10,000 MW Dextran Alexa488-conjugated (D-22910, Life Technologies) for 24 h. Organoids were fixed and stained by LTL without permeabilization. For nephrotoxicity assays, organoids at day 17 were cultured with 0, 5, 20 or 100 µM of Cisplatin (Sigma-Aldrich) for 24 h. The ratio of apoptotic proximal tubules to total proximal tubules was manually counted using ImageJ in 2 or 3 representative fields per experiment. In total, n=5 independent experiments. Images were taken using Zeiss LSM 780 confocal microscope.

Results & Discussion

Figure 7:
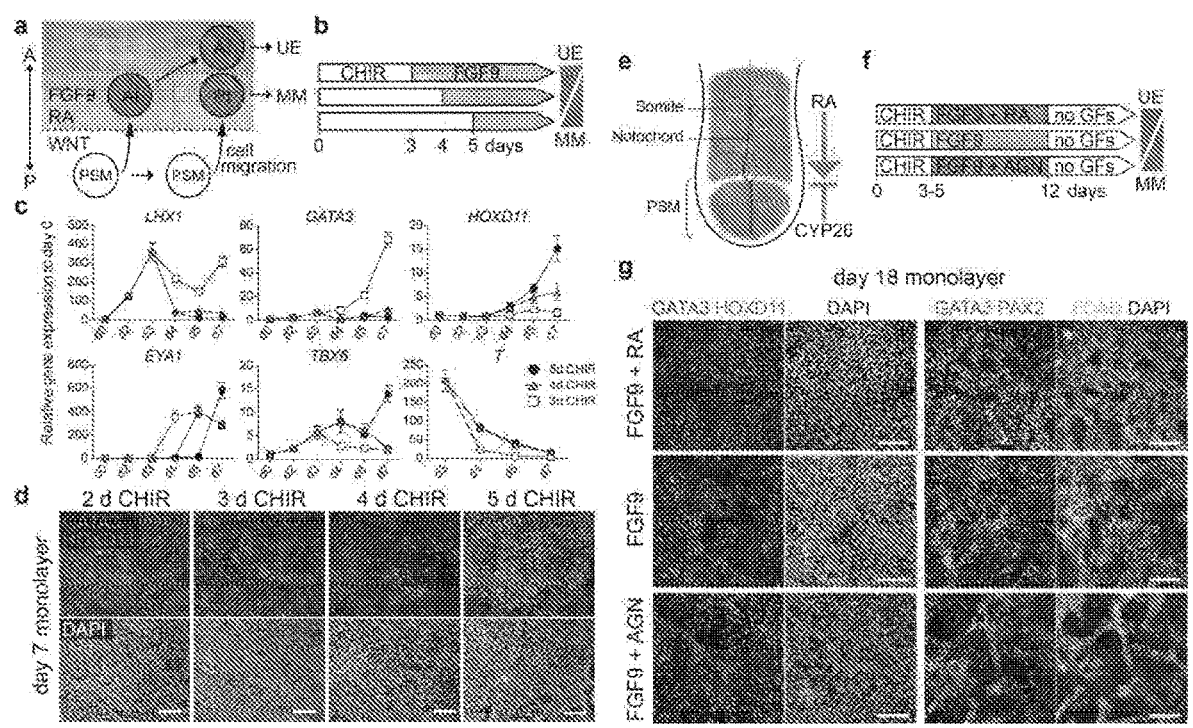
FIG. 7. Selective induction of either the collecting duct or kidney mesenchyme lineage. a, Schematic illustrating the mechanism of A-P patterning of the IM in the embryogenesis[13]. The timing of PSM cell migration determines the timing of the exposure to FGF9 and RA, resulting in fate selection between AI and PI. PSM, presomitic mesoderm. AI, anterior intermediate mesoderm; PI, posterior intermediate mesoderm; UE, ureteric epithelium; MM, metanephric mesenchyme. b, Schematic of three experimental timelines. c, Timecourse qPCR of an initial 7 days of the differentiation from the above timings. Experiments were conducted using monolayer culture condition. (mean±s.d., n=3 independent experiments) d, Immunofluorescence at day 7 of differentiation with the AI marker, GATA3, and the PI marker, HOXD11. Scale=100 μm. Experimental replicates=3 e, Schematic illustrating RA signaling post primitive streak stage. An RA-metabolizing enzyme, CYP26, is expressed in the PSM region to shield PSM cells from RA signaling. f, Schematic of three experimental timelines. RA or AGN193109 (AGN) were added with FGF9 after CHIR99021, followed by growth factor withdrawal (no GFs). Experiments were conducted with monolayer culture condition. g, Immunofluorescence at day 18 of differentiation from 3 days CHIR99021 followed by ±RA/AGN. AGN inhibited the AI specification of early migrating cells, causing posteriorization. At day 18, GATA3 and HOXD11 mark the UE and the MM respectively (left panels). GATA3$^+$ PAX2$^+$ECAD$^+$ cells represent the UE whereas GATA3$^-$ PAX2$^+$ cells do the MM (ECAD$^-$) and its derivatives (ECAD$^+$) (right panels). Experimental replicates=3. Scale=100 μm.

We have previously demonstrated in vitro that formation of the IM required FGF9 or FGF2[1]. Hence, in vivo we have assumed the UE forms from early migrating PSM cells exposed to FGF9 and RA soon after the primitive streak stage, while cells late to migrate, and hence exposed to longer Wnt signaling, should give rise to the MM[13] (FIG. 7a). To confirm this and further to the data shown in Example 1, we varied the duration of initial Wnt signaling (CHIR99201) prior to addition of FGF9 (FIG. 7b) and monitored markers of the AI and PI by qPCR. A shorter period of CHIR99021 induced the AI markers, LHX1 and GATA3, while longer days of CHIR99021 increased PI markers, HOXD11 and EYA1, at day 7. Prolonged expression of the PSM markers, TBX6 and T, after longer days in CHIR99021 suggested a delay in FGF9-induced fate commitment (FIG. 7c), as predicted. Immunofluorescence analysis showed that a longer (or shorter) duration of CHIR99021 induced less (more) AI but more (less) PI, as indicated by GATA3 and HOXD11 respectively at day 7 of differentiation (FIG. 7d). These observations persisted after 18 days of culture, with dominant UE induction (GATA3$^+$PAX2$^+$ ECAD$^+$) after fewer days in CHIR99201 and preferential induction of MM (PAX2$^+$ECAD$^-$) and its derivatives (PAX2$^+$ECAD$^+$) with longer days in CHIR66201. Further, we investigated whether RA signaling also controls A-P fate patterning of the IM using RA or an RAR antagonist, AGN193109, together with FGF9 (FIG. 7e, f). RA promoted UE induction whereas AGN193109 inhibited UE but enhanced induction of the MM lineage (FIG. 7g, h).

Figure 8:
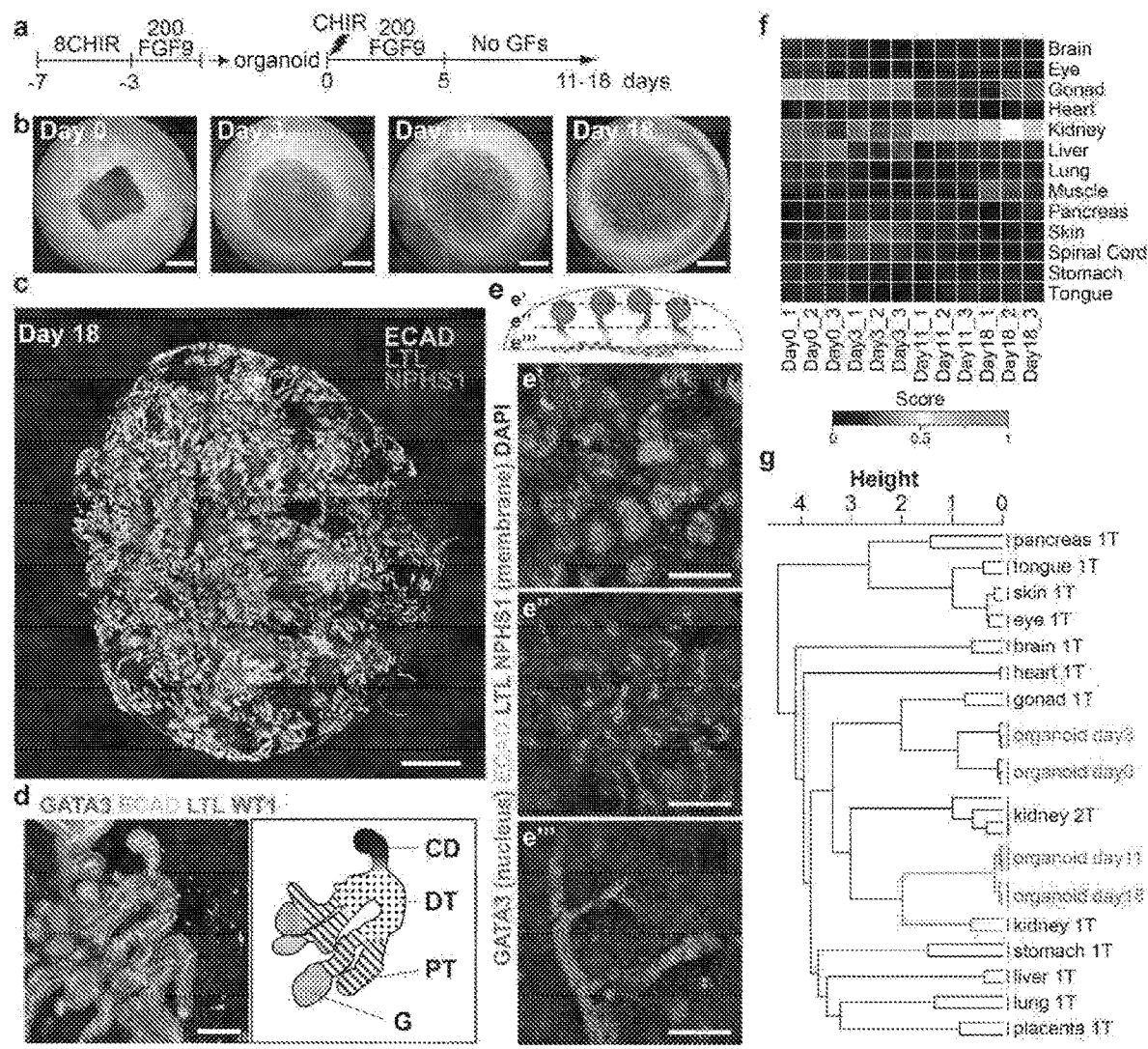
FIG. 8. Generating a kidney organoid equivalent to the human fetal kidney in vitro. a, Schematic of the differentiation protocol from hPSCs. b, Global brightfield observations of self-organizing kidney organoids across a time series. The success rate of organoid differentiation was 94.2% (138 organoids, 5 experiments). Scale=1 mm. c, Tile scan immunofluorescence of a whole kidney organoid displaying structural complexity. Scale=1 mm d, High power immunofluorescence microscopy showing a nephron segmented into 4 compartments, including the collecting duct (CD, GATA3$^+$ECAD$^+$), distal tubule (DT, GATA3$^-$ECAD$^+$LTL$^-$), proximal tubule (PT, ECAD$^-$LTL$^+$) and the glomerulus (G, WT1$^+$). Scale=100 μm. e, Confocal microscopy generating serial z-stack images from the bottom to the top of a day 11 kidney organoid (Extended Data Video 1 and 2). Schematic illustrates the position of different structures within an organoid. e', e'' and e''' are representative images taken through the organoids at the position indicated in e. Each segment of the nephron is marked (or colored in schematic) as described below: collecting ducts, GATA3$^+$ ECAD$^+$ (green dots in yellow); distal tubules, ECAD$^+$ (yellow); proximal tubules, LTL$^+$ (red): glomeruli, NPHS1 (green circles). Scale=100 μm. f, Heat map visualizing the relative transcriptional identity (score from 0 to 1 determined using the KeyGene algorithm[15]) of kidney organoids to 13 human fetal tissues. RNA-seq was performed on whole kidney organoids from 4 time points (day 0, 3, 11, 18 post aggregation)×3 individual organoids from 1 experiment/timepoint (See Supplementary Table 2). g, A dendrogram showing the hierarchical clustering of day 0, 3, 11 and 18 kidney organoids with human fetal organs from both first trimester and second trimester, based upon 85 key genes (Supplementary Table 3) previously defined[15]. This clearly shows a close match with Trimester 1 fetal kidney from day 11 and 18 of culture.

These results increase our understanding of embryogenesis as well as providing a method by which to modulate the relative induction of each of the two IM-derived progenitor populations essential for kidney formation. As a result, we modified our existing kidney differentiation process to increase the proportion of MM formed, increase the time in 3D culture and actively trigger nephron formation. This optimized approach was applied to either hESC or human iPSC and involved an initial 4 days of CHIR99021, which resulted in the induction of both the UE and MM in monolayer culture, followed by 3 days of FGF9 before transfer to organoid culture (FIG. 8a). The resulting aggregates were cultured for up to 20 days, during which time they spontaneously formed complex kidney organoids (FIG. 8b). During normal kidney development, nephron formation from the MM is initiated in response to Wnt9b secreted from the UE. In the mouse, ectopic nephron formation can be triggered via the addition of canonical Wnt agonists[14]. Indeed, maximal nephron number per organoid required a pulse of CHIR99021 for one hour after forming a pellet (FIG. 8a and FIG. 11a). In addition, the continued presence of FGF9 post this CHIR99021 pulse was essential for nephrogenesis, suggesting an additional role for FGF signaling after Wnt-mediated nephron induction (FIG. 11b) Within each organoid, the nephrons appropriately segmented into 4 components, including the collecting duct (GATA3$^+$ECAD$^+$), the early distal tubule (GATA3$^-$LTL$^-$ECAD$^+$). early proximal tubule (LTL$^+$ECAD$^-$) and the glomerulus (WT1$^+$) (FIG. 8c, d). Moreover, kidney organoids showed complex morphogenetic patterning with collecting duct trees forming at the bottom of the organoid, connecting to distal and proximal tubules in the middle, with the glomeruli at the top of each organoid (FIG. 8e', e", e'''). This patterning mimics the tissue organization observed in vivo where glomeruli arise in the cortex whereas the collecting ducts radiate through the organ from the middle. Here again, the relative level of collecting duct versus nephron within individual organoids could be varied with the timing of the initial CHIR99201-to-FGF9 switch. Next, we performed RNA sequencing of whole kidney organoids at day (d) 0, 3, 11 and 18 after aggregation and 3D culture. Across this timecourse we observed a temporal loss of nephron progenitor gene expression but an increase in markers of multiple nephron segments, including the podocytes, proximal and distal tubules (FIG. 12). Transcriptional profiling was performed and compared using an unbiased method with human fetal transcriptional datasets from 21 human fetal organs/tissues from the first and/or second trimester of pregnancy[15]. This analysis clustered kidney organoids at d11 and d18 of culture with first trimester human fetal kidney (FIG. 8f, g: FIG. 13). At the earlier culture timepoints (d0, d3), organoids more closely matched the fetal gonad, an embryologically closely related tissue also derived from the IM.

In a kidney, the epithelial cell types (nephron and collecting duct) are surrounded by a renal interstitium (stroma) within which there is a vascular network.

Figure 9:
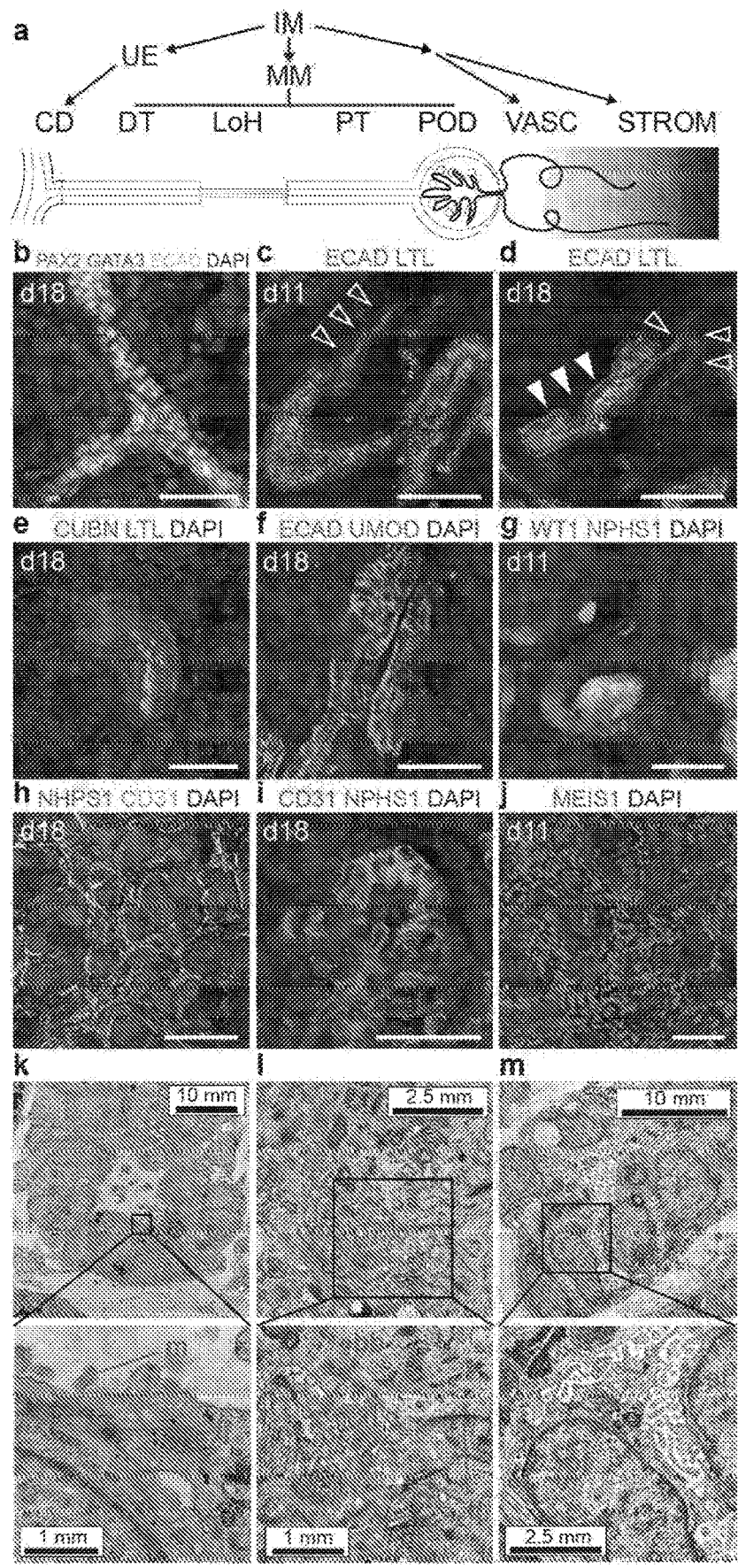
FIG. 9. Kidney organoids contain differentiating nephrons, stroma and vasculature with progressive maturation with time in culture.

As well as forming the MM, the IM gives rise to stromal and vascular progenitors (FIG. 9a)[16,17]. We examined kidney organoids for evidence of additional cell types and evidence of functional maturation. Collecting ducts could be distinguished based on co-expression of PAX2, GATA3 and ECAD (FIG. 9b). At d11, nephron epithelia showed proximal (LTL$^+$ECAD$^-$) and distal (LTL$^-$ECAD$^+$) elements (FIG. 9c). By d18, proximal tubules matured to co-express LTL with ECAD, with Cubilin evident on the apical surface (FIG. 9d, e). Transmission electron microscopy (TEM)

showed distinct epithelial subtypes; cells with few short microvilli surrounding an open lumen characteristic of collecting duct/distal tubule (FIG. 9k) and typical proximal tubular epithelium displaying an apical brush border with tight junctions (FIG. 9l). By d18, loops of Henle (UMOD$^+$) began to form (FIG. 9f). By d11, WT1$^+$NPHS1$^+$early glomeruli[18] comprising a Bowman's capsule with central podocyte formation was seen connected to proximal tubules (FIG. 9g). Kidney organoids also developed a CD31$^+$KDR$^-$SOX17$^+$ endothelial network with lumen formation (FIG. 9h). TEM showed the presence of primary and secondary foot processes characteristic of podocytes (FIG. 9m). In a developing kidney, renal interstitium differentiates into pericytes and mesangial cells[19]. As expected, kidney organoids contained PDGFRA$^+$ perivascular cells that lie along KDR$^+$ endothelia and PDGFRA$^+$ early mesangial cells invaginating the glomeruli (FIG. 14a, b), as observed in human fetal kidney[20]. Early avascular glomeruli contained basement membrane, as indicated by Laminin staining and TEM, and showed attaching foot processes on the basement membrane In some instances, glomeruli showed evidence of endothelial invasion (FIG. 9i), a feature never observed in explanted embryonic mouse kidneys[21]. Finally, nephrons were surrounded by MEIS1$^+$ renal interstitial cells, some of which were also FOXD1$^+$(FIG. 9j), suggesting the presence of cortical (FOXD1$^+$MEIS1$^+$) and medullary (FOXD1$^-$MEIS1$^+$) stroma. Hence, all anticipated kidney components form, pattern and begin to mature within these hPSC-derived kidney organoids. Consistent with these observations were the transcriptional changes across time in culture, with a gradual reduction in the nephrogenic mesenchyme and ureteric tip markers followed by the upregulation of genes specific to podocyte, proximal tubule, distal tubule and loop of Henle[23,24] (FIG. 11).

The utility of stem-cell derived kidney organoids for disease modelling or drug screening will be dependent upon the functional maturation of the nephrons within these organoids. To test this, we focused on the proximal tubules, a nephron segment that plays important roles in solute, vitamin, hormone and amino acids reabsorption. The capacity of Cubilin-mediated proximal tubule specific endocytosis was demonstrated by the selective uptake of Dextran-Alexa488 from the media by the LTL$^+$tubules after 24 hours of exposure (FIG. 10a). The proximal tubules represent a particular target for nephrotoxicity due to the expression of multidrug resistance (such as ABCB1, ABCG2) and anion and cation transporters (such as the SLC22 gene family)[23,24]. Cisplatin is one of such nephrotoxicant that induces Caspase-mediated acute apoptosis of proximal tubular cells in the kidney[25,26]. We treated kidney organoids with 0, 5 and 20 µM Cisplatin for 24 hours before examining cleaved-CASP3 antibody staining. While control organoids showed occasional apoptotic interstitial cells, both 5 µM and 20 µM Cisplatin induced specific acute apoptosis in mature proximal tubular cells (LTL$^+$ECAD$^+$), whereas immature cells (LTL$^+$ECAD$^-$) did not undergo apoptosis (FIG. 10b, c).

In summary, this study demonstrates that by carefully balancing A/P patterning of IM with small molecules it is possible to direct human pluripotent stem cells to form a complex multicellular kidney organoid that comprises fully segmented nephrons surrounded by endothelia and renal interstitium and is transcriptionally similar to a human fetal kidney. As such, these will improve our understanding of human kidney development. Each kidney organoid reaches a substantial size with >500 nephrons per organoid, a number equivalent to a mouse kidney at 14.5 dpc[27]. While there is room for further improvement with regard to tubular functional maturity, glomerular vascularisation and a contiguous collecting duct epithelium with a single exit path for urine, the tissue complexity and degree of organoid functionalization observed here supports their use to screen drugs for toxicity, modelling genetic kidney disease or act as a source of specific kidney cell types for cellular therapy.

The fact that we can form organoids from differentiated hES cell cultures alone opens the possibility of generating tissue-based nephrotoxicity screens, in vitro disease models or developing transplantable organoids to supplement renal function. It also suggests the feasibility of generating specific mature renal cell types for later purification.

Particular uses of the cells generated using this method may include:
  Generating mini-kidney organoids or purified renal cell for nephrotoxicity screening:
  Generating mini-kidney organoids or purified renal cell for disease modelling, either in general or patient by patient; and/or
  Generating mini-kidney organoids or purified renal cell types for drug screening for the therapeutic treatment of kidney disease.

These could be performed in microbioreactors or after bioprinting into a larger format screen. For disease modelling or drug screening, it is likely we would purify individual cell types and culture them in a manner or format that would provide useful information based upon the specific disease. For example, we might isolate UB and grow in matrigel cultures to assess cyst formation (e.g. for diseases such as nephronopthisis) or isolate MM to make podocytes (e.g. for diseases such as Finnish nephropathy or Alport syndrome).

Particular examples of cellular therapies and organ replacement or repair may include:
  Generating kidney cell types for cellular therapy (acute kidney injury or chronic kidney injury):
  Generating kidney cell types for whole organ replacement bioengineering, which may need to link together multiple smaller kidneys to form a replacement 'organ'; and/or
  Generating kidney cell types for recellularisation of decellularised scaffolds.

Further applications include:
1) Generation of kidney organoids from human pluripotent stem cell lines engineered to report one or more fluorescent reporters as readouts of differentiation to specific renal cell types. This would allow the generation from a single starting cell line an organoid that would both report the degree of differentiation complexity without the requirement of specific antibody visualisation and would facilitate combinatorial FACS sorting to purify a variety of specific renal cell types from the one differentiation. Such sorted cells might be of use in cellular therapy.
2) Generation of kidney organoids from human pluripotent stem cell lines engineered to report one or more fluorescent or luciferase based reporters as readouts of cellular injury (predicted responses to nephrotoxicity, cytotoxicity or induction of apoptosis/necrosis). This would allow the generation of organoids for drug or nephrotoxicity screening with a quantifiable readout of response.
3) Generation of either collecting duct alone or metanephric mesenchyme alone for combination with other bioprinted structures. For example, the generation of nephron-forming mesenchyme alone for combination with collecting duct cells differentiated separately but bioprinted into a ureteric tree. The advantage here would be the creation of a specifically patterned collecting duct network around which nephrons could differentiate such that the final product could act as a transplantable organ capable of directing urine to a single exit.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

TABLE 1

Reagent sources

| Reagent | Catalogue Number | Supplier |
|---|---|---|
| Gelatin | G9391 | Sigma Aldrich |
| bFGF | GF003-AF | Merck |
| FGF9 | 273-F9-025 | R&D |
| CHIR99021 | 4423/10 | R&D |
| Heparin | H4784-250 MG | Sigma-Aldrich |
| hESC qualified Matrigel | FAL354277 | In Vitro Technologies |
| TrypLE Select | 12563029 | Life Technologies |
| Trypsin EDtA (0.25 %) | 25200-072 | Life Technologies |
| APEL Media | 05210 | Stem Cell Technologies |
| Antibiotic-Antimycotic (100X) | 15240-062 | Life Technologies |
| DMEM/F-12 | 11320-082 | Life Technologies |
| DMEM high glucose | 11995-073 | Life Technologies |
| Foetal Bovine Serum | SFBSF | Interpath Services |
| Penicillin/Streptomycin | 15070-063 | Life Technologies |
| Paraformaldehyde | 30525-89-4 | Sigma-Aldrich |
| Donkey serum | D9663-10 ML | Sigma-Aldrich |
| Triton X400 | 19284 | Sigma-Aldrich |

| Cell line | Catalogue Number | Supplier |
|---|---|---|
| C32 human iPSC | N/A | Dr. Wolvetang at UQ (AIBN) |
| Primary mouse embryonic fibroblasts | PMEF-CFL | Merck |

| Antibodies | Catalogue Number | Supplier |
|---|---|---|
| ECAD | 610181 | BD-Bioscience |
| GATA3 | AF2605 | R&D Systems |
| NPHS1 | 4F4269 | R&D Systems |
| WT1 | SC-192 | Santa Cruz Biotechnology |
| LTL - biotin conjugated | B-1325 | Vector Laboratories |
| Secondary | Alexa Fluor (Donkey) | Life Technologies |

TABLE 2

Sequences of primers used for qRTPCR

| | Forward (5'-3') | Reverse (5'-3') |
|---|---|---|
| T | AGGTACCCAACC CTGAGGA (SEQ ID NO: 1) | GCAGGTGAGTTG TCAGAATAGGT (SEQ ID NO: 2) |
| LHX1 | ATGCAACCTGAC CGAGAAGT (SEQ ID NO: 3) | CAGGTCGCTAGG GGAGATG (SEQ ID NO: 4) |
| TBX6 | CATCCACGAGAA TTGTACCCG (SEQ ID NO: 5) | AGCAATCCAGTT TAGGGGTGT (SEQ ID NO: 6) |
| GATA3 | GCCCCTCATTAA GCCCAAG (SEQ ID NO: 7) | TTGTGGTGGTCT GACAGTTCG (SEQ ID NO: 8) |
| HOXD11 | GCCAGTGTGCTG TCGTTCCC (SEQ ID NO: 9) | CTTCCTACAGAC CCCGCCGT (SEQ ID NO: 10) |
| EYA1 | ATCTAACCAGCC CGCATAGC (SEQ ID NO: 11) | GTGCCATTGGGA GTCATGGA (SEQ ID NO: 12) |
| GAPDH | AGCCACATCGCT CAGACAC (SEQ ID NO: 13) | GCCCAATACGAC CAAATCC (SEQ ID NO: 14) |

TABLE 3

| Ensembl Gene ID | Gene Name | Chromosome | Organ |
|---|---|---|---|
| ENSG00000105398 | SULT2A1 | 19 | Adrenal |
| ENSG00000109132 | PHOX2B | 4 | Adrenal |
| ENSG00000136931 | NR5A1 | 9 | Adrenal |
| ENSG00000147256 | ARHGAP36 | X | Adrenal |
| ENSG00000148795 | CYP17A1 | 10 | Adrenal |
| ENSG00000153002 | CPB1 | 3 | Adrenal |
| ENSG00000000005 | TNMD | X | Amnion |
| ENSG00000094755 | GABRP | 5 | Amnion |
| ENSG00000115221 | ITGB6 | 2 | Amnion |
| ENSG00000128709 | HOXD9 | 2 | Amnion |
| ENSG00000134258 | VTCN1 | 1 | Amnion |
| ENSG00000167916 | KRT24 | 17 | Amnion |
| ENSG00000125462 | C1orf61 | 1 | Brain |
| ENSG00000130287 | NCAN | 19 | Brain |
| ENSG00000170370 | EMX2 | 10 | Brain |
| ENSG00000186487 | MYT1L | 2 | Brain |
| ENSG00000197757 | HOXC6 | 12 | Brain |
| ENSG00000106366 | SERPINE1 | 7 | Chorion |
| ENSG00000185269 | NOTUM | 17 | Chorion |
| ENSG00000196126 | HLA-DRB1 | 6 | Chorion |
| ENSG00000196136 | SERPINA3 | 14 | Chorion |
| ENSG00000080166 | DCT | 13 | Eye |
| ENSG00000137273 | FOXF2 | 6 | Eye |
| ENSG00000147655 | RSPO2 | 8 | Eye |
| ENSG00000180660 | MAB21L1 | 13 | Eye |
| ENSG00000185960 | SHOX | X | Eye |
| ENSG00000104435 | STMN2 | 8 | Gonad |
| ENSG00000115596 | WNT6 | 2 | Gonad |
| ENSG00000143355 | LHX9 | 1 | Gonad |
| ENSG00000143954 | REG3G | 2 | Gonad |
| ENSG00000184937 | WT1 | 11 | Gonad |
| ENSG00000242349 | NPPA-AS1 | 1 | Heart A |
| ENSG00000160808 | MYL3 | 3 | Heart V |
| ENSG00000112818 | MEP1A | 6 | Intestine |
| EN5G00000173702 | MUC13 | 3 | Intestine |
| ENSG00000181541 | MAB21L2 | 4 | Intestine |
| ENSG00000074803 | SLC12A1 | 15 | Kidney |
| ENSG00000075891 | PAX2 | 10 | Kidney |
| ENSG00000116218 | NPHS2 | 1 | Kidney |
| ENSG00000055957 | ITIH1 | 3 | Liver |
| EN5G00000091513 | TF | 3 | Liver |
| ENSG00000132855 | ANGPTL3 | 1 | Liver |
| ENSG00000162365 | CYP4A22 | 1 | Liver |
| ENSG00000164265 | SCGB3A2 | 5 | Luna |
| ENSG00000262152 | LINC00514 | 16 | Lung |
| ENSG00000106511 | MEOX2 | 7 | Mother |
| ENSG00000162706 | CADM3 | 1 | Mother |
| ENSG00000164825 | DEFB1 | 8 | Mother |

TABLE 3-continued

| Ensembl Gene ID | Gene Name | Chromosome | Organ |
|---|---|---|---|
| ENSG00000166426 | CRABP1 | 15 | Mother |
| EN5G00000172179 | PRL | 6 | Mother |
| ENSG00000189058 | APOD | 3 | Mother |
| ENSG00000000005 | TNNID | X | Muscle |
| ENSG00000122180 | MYOG | 1 | Muscle |
| ENSG00000180818 | HOXC10 | 12 | Muscle |
| .ENSG00000114204 | SERPINI2 | 3 | Pancreas |
| ENSG00000130675 | MNX1 | 7 | Pancreas |
| ENSG00000139515 | PDX1 | 13 | Pancreas |
| ENSG00000255245 | FXYD6-FXYD2 | 11 | Pancreas |
| ENSG00000006659 | LGALS14 | 19 | Placenta |
| ENSG00000128918 | ALDH1A2 | 15 | Placenta |
| ENSG00000164707 | SLC13A4 | 7 | Placenta |
| ENSG00000170498 | KISS1 | 1 | Placenta |
| ENSG00000092607 | TBX15 | 1 | Skin |
| EN5G00000121742 | GTB6 | 13 | Skin |
| ENSG00000147655 | RSPO2 | 8 | Skin |
| ENSG00000167768 | KRT1 | 12 | Skin |
| ENSG00000188508 | KRTDAP | 19 | Skin |
| ENSG00000262152 | LINC00514 | 16 | Skin |
| ENSG00000052344 | PRSS8 | 16 | Sp. Cord |
| ENSG00000120068 | HOXB8 | 17 | Sp. Cord |
| ENSG00000177551 | NHLH2 | 1 | Sp. Cord |
| ENSG00000073754 | CD5L | I | Spleen |
| ENSG00000133135 | RNF128 | X | Spleen. |
| ENSG00000136931 | NR5A1 | 9 | Spleen |
| EN5G00000066405 | CLDN18 | 3 | Stomach |
| ENSG00000131668 | BARX1 | 9 | Stomach |
| ENSG00000134812 | OF | 11 | Stomach |
| ENSG00000184956 | MUC6 | 11 | Stomach |
| EN5G00000112936 | C7 | 5 | Tongue |
| ENSG00000133055 | MYBPH | 1 | Tongue |
| EN5G00000169469 | SPRR1B | 1 | Tongue |
| EN5G00000052850 | ALX4 | 11 | Umb. Cord |
| ENSG00000077279 | DCX | X | Umb. Cord |
| ENSG00000089199 | CHGB | 20 | Umb. Cord |
| ENSG00000156076 | WIF1 | 17 | Umb. Cord |
| ENSG00000164093 | PITX2 | 4 | Umb. Cord |
| ENSG00000166426 | CRABP1 | 15 | Umb. Cord |
| ENSG00000172209 | GPR22 | 7 | Umb. Cord |
| ENSG00000187957 | DNER | 2 | Umb. Cord |
| ENSG00000253293 | HOXA10 | 7 | Umb. Cord |

REFERENCES

1. Takasato, M. et al. Directing human embryonic stem cell differentiation towards a renal lineage generates a self-organizing kidney. Nat. Cell Biol. 16, 118-26 (2014).
2. James, R. G. & Schultheiss, T. M. Patterning of the Avian Intermediate Mesoderm by Lateral Plate and Axial Tissues. Dev. Biol. 253, 109-124 (2003).
3. Mae, S. et al. Monitoring and robust induction of nephrogenic intermediate mesoderm from human pluripotent stem cells. Nat. Commun. 4, 1367 (2013).
4. Xia, Y. et al. Directed differentiation of human pluripotent cells to ureteric bud kidney progenitor-like cells. Nat. Cell Biol. 15, 1507-15 (2013).
5. Taguchi. A. et al. Redefining the in vivo origin of metanephric nephron progenitors enables generation of complex kidney structures from pluripotent stem cells. Cell Stem Cell 14, 53-67 (2014).
6. Lam, A. Q. et al. Rapid and Efficient Differentiation of Human Pluripotent Stem Cells into Intermediate Mesoderm That Forms Tubules Expressing Kidney Proximal Tubular Markers. J. Am. Soc. Nephrol. 25, 1211-1225 (2014).
7. Kang, M. & Han, Y. Differentiation of human pluripotent stem cells into nephron progenitor cells in a serum and feeder free system. PLoS One 9, e94888 (2014).
8. Xu, J. et al. Eyal interacts with Six2 and Myc to regulate expansion of the nephron progenitor pool during nephrogenesis. Dev. Cell 31, 434-47 (2014).
9. Duester, G. Retinoic acid synthesis and signaling during early organogenesis. Cell 134, 921-31 (2008).
10. Sakai, Y. et al. The retinoic acid-inactivating enzyme CYP26 is essential for establishing an uneven distribution of retinoic acid along the anterio-posterior axis within the mouse embryo. Genes Dev. 15, 213-25 (2001).
11. Abu-Abed, S. et al. The retinoic acid-metabolizing enzyme, CYP26A, is essential for normal hindbrain patterning, vertebral identity, and development of posterior structures. Genes Dev. 15, 226-40 (2001).
12. Sweetman, D., Wagstaff. L., Cooper, O., Weijer, C. & Minsterberg, A. The migration of paraxial and lateral plate mesoderm cells emerging from the late primitive streak is controlled by different Wnt signals. BMC Dev. Biol. 8, 63 (2008).
13. Takasato, M. & Little. M. H. The origin of the mammalian kidney: implications for recreating the kidney in vitro. Development 142, 1937-1947 (2015).
14. Park, J. et al. Six2 and Wnt regulate self-renewal and commitment of nephron progenitors through shared gene regulatory networks. Dev. Cell 23, 637-51 (2012).
15. Roost. M. S. et al. KeyGenes, a Tool to Probe Tissue Differentiation Using a Human Fetal Transcriptional Atlas. Stem Cell Reports 4, 1112-1124 (2015).
16. Mugford, J. W., Sipilä, P., McMahon, J. A. & McMahon, A. P. Osr1 expression demarcates a multi-potent population of intermediate mesoderm that undergoes progressive restriction to an Osr1-dependent nephron progenitor compartment within the mammalian kidney. Dev. Biol. 324, 88-98 (2008).
17. Sims-Lucas, S. et al. Endothelial Progenitors Exist within the Kidney and Lung Mesenchyme. PLoS One 8, 1-8 (2013).
18. Brunskill, E. W., Georgas, K., Rumballe, B., Little, M. H. & Potter, S. S. Defining the molecular character of the developing and adult kidney podocyte. PLoS One 6, (2011).
19. Kobayashi, A. et al. Identification of a Multipotent Self-Renewing Stromal Progenitor Population during Mammalian Kidney Organogenesis. Stem Cell Reports 3, 650-662(2014).
20. Floege, J. et al. Localization of PDGF alpha-receptor in the developing and mature human kidney. Kidney Int. 51, 1140-1150 (1997).
21. Loughna, S., Yuan, H. T. & Woolf, A. S. Effects of oxygen on vascular patterning in Tie1/LacZ metanephric kidneys in vitro. Biochem. Biophys. Res. Commun. 247, 361-6 (1998).
22. Brunskill, E. W. et al. Atlas of gene expression in the developing kidney at microanatomic resolution. Dev. Cell 15, 781-91 (2008).
23. Thiagarajan, R. D., et al. Identification of anchor genes during kidney development defines ontological relationships, molecular subcompartments and regulatory pathways. PLoS One. 6(2):e17286 (2011).
24. Cheng, X. & Klassen. C. D. Tissue distribution, ontogeny, and hormonal regulation of xenobiotic transporters in mouse kidneys. Drug Metab. Dispos. 37, 2178-85 (2009)
25. Mese, H., Sasaki, A., Nakayama, S., Alcalde, R. E. & Matsumura, T. The role of caspase family protease, caspase-3 on cisplatin-induced apoptosis in cisplatin-resistant A431 cell line. Cancer Chemother. Pharmacol. 46, 241-245 (2000).

26. Cummings, B. S. & Schnellmann, R. G. Cisplatin-induced renal cell apoptosis: caspase 3-dependent and —independent pathways. *J. Pharmacol. Exp. Ther.* 302, 8-17 (2002).
27. Short, K. M. et al. Global quantification of tissue dynamics in the developing mouse kidney. *Dev. Cell* 29, 188-202 (2014).
28. Briggs, J. A. et al. Integration-free induced pluripotent stem cells model genetic and neural developmental features of down syndrome etiology. *Stem Cells* 31, 467-78 (2013).
29. Dobin, A. et al. STAR: Ultrafast universal RNA-seq aligner. *Bioinformatics* 29, 15-21 (2013).
30. Love, M. I., Huber, W. & Anders, S. Moderated estimation of fold change and dispersion for RNA-seq data with DESeq2. *Genome Biol.* 15, 550 (2014).
31. Orlova V V, van den Hil F E, Petrus-Reurer S, Drabsch Y, Ten Dijke P, Mummery CL. Generation, expansion and functional analysis of endothelial cells and pericytes derived from human pluripotent stem cells. *Nat Protoc.* 2014; 9(6):1514-31.

The invention claimed is:

1. A method of producing one or more renal organoids comprising:
   (a) differentiating intermediate mesoderm (IM) cells into nephron progenitor cells and ureteric epithelial progenitor cells by contacting the IM cells with a Wnt agonist, fibroblast growth factor 9 (FGF9), and one or more compounds selected from the group consisting of bone morphogenic protein 7 (BMP7), heparin, retinoic acid (RA), an RA analog, an RA agonist, and an RA antagonist, wherein the RA antagonist increases the relative production of nephron progenitor cells from the IM cells; and
   (b) culturing the nephron progenitor cells and ureteric epithelial progenitor cells under conditions that induce aggregation of the nephron progenitor cells and ureteric epithelial progenitor cells into one or more renal organoids that are at least partly vascularized and/or comprise vascular progenitors, wherein the vascularization is facilitated by conditions that promote or direct development of vascular endothelium or vascular progenitors from mesenchymal cells or tissues.

2. The method of claim 1, wherein the RA analog or the RA agonist increases the relative production of ureteric epithelial progenitor cells from the IM cells.

3. The method of claim 1, wherein the Wnt agonist increases the relative production of nephron progenitor cells from the IM cells.

4. The method of claim 1, wherein the nephron progenitor cells and ureteric epithelial progenitor cells are produced synchronously or simultaneously from the IM cells.

5. The method of claim 1, further comprising contacting posterior primitive streak cells with one or more agents that facilitate differentiation of the posterior primitive streak cells into said IM cells.

6. The method of claim 5, further comprising contacting human pluripotent stem cells (hPSCs) with one or more agents that facilitate differentiation of the hPSCs into said posterior primitive streak cells.

7. The method of claim 1, wherein the Wnt agonist is CHIR99021.

8. The method of claim 1, wherein the IM cells are (i) first contacted with the Wnt agonist and (ii) then contacted with the FGF9.

9. The method of claim 8, wherein the Wnt agonist is CHIR99021.

10. The method of claim 8, further comprising (iii) contacting the cells resulting from step (ii) with a Wnt agonist.

11. The method of claim 10, wherein the Wnt agonist in step (i) is CHIR99021.

12. The method of claim 10, wherein the Wnt agonist in step (iii) is CHIR99021.

13. The method of claim 10, wherein the Wnt agonist in step (i) is CHIR99021 and the Wnt agonist in step (iii) is CHIR99021.

14. The method of claim 13, wherein the concentration of the Wnt agonist in step (i) is about 1-20 μM, the concentration of FGF9 is about 100-300 ng/ml, and the concentration of the Wnt agonist in step (iii) is about 1-15 μM.

15. The method of claim 14, wherein the concentration of the Wnt agonist in step (i) is 5-15 μM.

16. The method of claim 1, wherein the one or more compounds is heparin.

17. The method of claim 16, wherein the IM cells are (i) first contacted with the Wnt agonist and (ii) then contacted with the FGF9 and the heparin.

18. The method of claim 17, wherein the Wnt agonist is CHIR99021.

19. The method of claim 17, further comprising (iii) contacting the cells resulting from step (ii) with a Wnt agonist.

20. The method of claim 19, wherein the Wnt agonist in step (i) is CHIR99021.

21. The method of claim 19, wherein the Wnt agonist in step (iii) is CHIR99021.

22. The method of claim 19, wherein the Wnt agonist in step (i) is CHIR99021 and the Wnt agonist in step (iii) is CHIR99021.

23. The method of claim 22, wherein the concentration of the Wnt agonist in step (i) is about 1-20 μM, the concentration of FGF9 is about 100-300 ng/ml, and the concentration of the Wnt agonist in step (iii) is about 1-15 μM.

24. The method of claim 23, wherein the concentration of the Wnt agonist in step (i) is 5-15 μM.

\* \* \* \* \*

UNITED STATES PATENT AND TRADEMARK OFFICE
CERTIFICATE OF CORRECTION

| | | |
|---|---|---|
| PATENT NO. | : 12,134,785 B2 | Page 1 of 1 |
| APPLICATION NO. | : 16/682541 | |
| DATED | : November 5, 2024 | |
| INVENTOR(S) | : Minoru Takasato et al. | |

It is certified that error appears in the above-identified patent and that said Letters Patent is hereby corrected as shown below:

In the Claims

Column 42, Claim 14, Line 43, delete "ng/ml;" and insert --ng/mL;--.

Column 42, Claim 23, Line 66, delete "ng/ml;" and insert --ng/mL;--.

Signed and Sealed this
Eleventh Day of November, 2025

John A. Squires
*Director of the United States Patent and Trademark Office*

```
                            SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Forward primer T

<400> SEQUENCE: 1
aggtacccaa ccctgagga                                                        19

<210> SEQ ID NO 2
<211> LENGTH: 23
<212> TYPE: DNA
<213> ORGANISM: Artificial Sequence
<220> FEATURE:
<223> OTHER INFORMATION: Reverse primer T

<400> SEQUENCE: 2
gcaggtgagt tgtcagaata ggt                                                   23

<210> SEQ ID NO 3
<211> LENGTH: 20
<212> TYPE: DNA
<213> ORGANISM: Artificial Sequence
<220> FEATURE:
<223> OTHER INFORMATION: Forward primer LHX1

<400> SEQUENCE: 3
atgcaacctg accgagaagt                                                       20

<210> SEQ ID NO 4
<211> LENGTH: 19
<212> TYPE: DNA
<213> ORGANISM: Artificial Sequence
<220> FEATURE:
<223> OTHER INFORMATION: Reverse primer LHX1

<400> SEQUENCE: 4
caggtcgcta ggggagatg                                                        19

<210> SEQ ID NO 5
<211> LENGTH: 21
<212> TYPE: DNA
<213> ORGANISM: Artificial Sequence
<220> FEATURE:
<223> OTHER INFORMATION: Forward primer TBX6

<400> SEQUENCE: 5
catccacgag aattgtaccc g                                                     21

<210> SEQ ID NO 6
<211> LENGTH: 21
```

```
<212> TYPE: DNA
<213> ORGANISM: Artificial Sequence
<220> FEATURE:
<223> OTHER INFORMATION: Reverse primer TBX6

<400> SEQUENCE: 6
agcaatccag tttaggggtg t                                              21

<210> SEQ ID NO 7
<211> LENGTH: 19
<212> TYPE: DNA
<213> ORGANISM: Artificial Sequence
<220> FEATURE:
<223> OTHER INFORMATION: Forward primer GATA3

<400> SEQUENCE: 7
gcccctcatt aagcccaag                                                 19

<210> SEQ ID NO 8
<211> LENGTH: 21
<212> TYPE: DNA
<213> ORGANISM: Artificial Sequence
<220> FEATURE:
<223> OTHER INFORMATION: Reverse primer GATA3

<400> SEQUENCE: 8
ttgtggtggt ctgacagttc g                                              21

<210> SEQ ID NO 9
<211> LENGTH: 20
<212> TYPE: DNA
<213> ORGANISM: Artificial Sequence
<220> FEATURE:
<223> OTHER INFORMATION: Forward primer HOXD11

<400> SEQUENCE: 9
gccagtgtgc tgtcgttccc                                                20

<210> SEQ ID NO 10
<211> LENGTH: 20
<212> TYPE: DNA
<213> ORGANISM: Artificial Sequence
<220> FEATURE:
<223> OTHER INFORMATION: Reverse primer HOXD11

<400> SEQUENCE: 10
cttcctacag accccgccgt                                                20

<210> SEQ ID NO 11
<211> LENGTH: 20
<212> TYPE: DNA
<213> ORGANISM: Artificial Sequence
<220> FEATURE:
<223> OTHER INFORMATION: Forward primer EYA1

<400> SEQUENCE: 11
atctaaccag cccgcatagc                                                20

<210> SEQ ID NO 12
<211> LENGTH: 20
<212> TYPE: DNA
<213> ORGANISM: Artificial Sequence
<220> FEATURE:
<223> OTHER INFORMATION: Reverse primer EYA1

<400> SEQUENCE: 12
```

```
gtgccattgg gagtcatgga                                              20

<210> SEQ ID NO 13
<211> LENGTH: 19
<212> TYPE: DNA
<213> ORGANISM: Artificial Sequence
<220> FEATURE:
<223> OTHER INFORMATION: Forward primer GAPDH

<400> SEQUENCE: 13
agccacatcg ctcagacac                                               19

<210> SEQ ID NO 14
<211> LENGTH: 19
<212> TYPE: DNA
<213> ORGANISM: Artificial Sequence
<220> FEATURE:
<223> OTHER INFORMATION: Reverse primer GAPDH

<400> SEQUENCE: 14
gcccaatacg accaaatcc                                               19
```